United States Patent [19]

Ostermayer et al.

[11] Patent Number: 4,727,067
[45] Date of Patent: * Feb. 23, 1988

[54] DERIVATIVES OF 3-AMINOPROPANE-1,2-DIOL

[75] Inventors: Franz Ostermayer; Markus Zimmermann, both of Riehen, Switzerland

[73] Assignee: Ciba-Geigy Corporation, Ardsley, N.Y.

[*] Notice: The portion of the term of this patent subsequent to Feb. 5, 2002 has been disclaimed.

[21] Appl. No.: 785,300

[22] Filed: Oct. 7, 1985

Related U.S. Application Data

[63] Continuation-in-part of Ser. No. 687,093, Dec. 27, 1984, Pat. No. 4,636,511, which is a continuation of Ser. No. 378,165, May 14, 1982, Pat. No. 4,497,813, which is a continuation-in-part of Ser. No. 255,414, Apr. 20, 1981, abandoned, which is a continuation-in-part of Ser. No. 181,581, Aug. 27, 1980, abandoned, which is a continuation-in-part of Ser. No. 122,640, Feb. 19, 1980, abandoned.

[30] Foreign Application Priority Data

Mar. 1, 1979 [CH] Switzerland ............ 2037/79

[51] Int. Cl.$^4$ .............. A61K 31/165; C07C 103/26
[52] U.S. Cl. ........................ 514/162; 564/156; 564/165
[58] Field of Search .............. 564/156, 165; 514/162

[56] References Cited

U.S. PATENT DOCUMENTS 4,636,511  1/1987  Ostermayer .................. 514/160

FOREIGN PATENT DOCUMENTS 151743  2/1985  Norway ........................ 514/162

Primary Examiner—Robert Gersil
Attorney, Agent, or Firm—Michael W. Glynn; Irving M. Fishman

[57] ABSTRACT

Derivatives of 3-aminopropane-1,2-diol of the formula

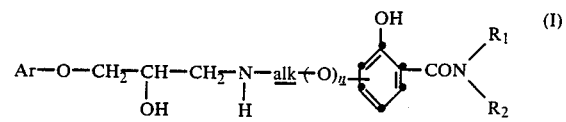

in which

Ar represents optionally substituted aryl, $n$ represents the number 0 or 1, and alk represents alkylene having 2 to 5 carbon atoms, the nitrogen atom and the oxygen atom, or, if $n$ is zero, the phenyl radical, being separated from one another by at least two carbon atoms, and $R_1$ and $R_2$, independently of one another, each represents hydrogen or lower alkyl, or together they represent lower alkylene, oxa-lower alkylene, thia-lower alkylene, aza-lower alkylene or N-lower alkyl-aza-lower alkylene, and salts of such compounds, processes for their manufacture, medicaments containing the new compounds and their use for the treatment of *Angina pectoris* and cardiac arrhythmia, and as blood pressure-reducing agents, as well as for the treatment of reactive or endogenic states of depression.

5 Claims, No Drawings

DERIVATIVES OF 3-AMINOPROPANE-1,2-DIOL

This is a continuation-in-part application of our copending application Ser. No. 687,093 filed Dec. 27, 1984 now U.S. Pat. No. 4,636,511, which in turn is a continuation application of our application Ser. No. 378,165 filed May 14, 1982, now U.S. Pat. No. 4,497,813, which in turn is a continuation-in-part application of our application Ser. No. 255,414 filed Apr. 20, 1981, now abandoned, which in turn is a continuation-in-part application of our application Ser. No. 181,581 filed Aug. 27, 1980, now abandoned, which in turn is a continuation-in-part application of our application Ser. No. 122,640 filed Feb. 19, 1980, now abandoned.

The invention relates to new derivatives of 3-aminopropane-1,2-diol, processes for their preparation, pharmaceutical preparations containing such compounds and their use for the manufacture of pharmaceutical preparations or as pharmacologically active compounds.

The new derivatives of 3-aminopropane-1,2-diol according to the invention corresponds to the formula

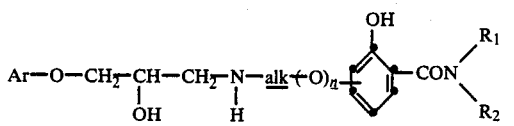

in which
Ar represents optionally substituted aryl,
n represents the integer 0 or 1, and
alk represents alkylene having from 2 to 5 carbon atoms, the nitrogen atom and the oxygen atom, or if n is zero, the phenyl radical, being separated from one another by at least two carbon atoms, and
$R_1$ and $R_2$, independently of one another, each represents hydrogen or lower alkyl, or together they represent lower alkylene, oxa-lower alkylene, thia-lower alkylene, aza-lower alkylene or N-lower alkyl-aza-lower alkylene.

The invention also relates to salts of these compounds.

An aryl radical Ar is a carbocyclic or heterocyclic aryl radical. Preferably, Ar is monocyclic or bicyclic carbocyclic aryl or monocyclic or bicyclic heteroaryl bonded by a ring carbon atom and containing as ring members a maximum of two nitrogen atoms and/or one oxygen or sulphur atom. These radicals may be unsubstituted or substituted one or more times, preferably at most three times, and in bicyclic radicals Ar, the ring not directly bonded to the ether group may be at least partially hydrogenated and in this case may be substituted especially by oxo. Ar is especially phenyl, or also naphthyl, such as 1-naphthyl, or partially saturated naphthyl, such as 1,2,3,4-tetrahydro-5-naphthyl; when Ar represents monocyclic or bicyclic heteroaryl it is especially pyridyl, for example, pyrid-2-yl, pyrid-3-yl or pyrid-4-yl, pyridazinyl, for example pyridazin-3-yl, pyrimidinyl, for example pyrimidin-2-yl or pyrimidin-4-yl, pyrazinyl, e.g. pyrazin-2-yl, thienyl, for example thien-3-yl, thiazolyl, e.g. thiazol-2-yl, thiadiazolyl, e.g. 1,2,4-thiadiazol-3-yl or -5-yl or 1,2,5-thiadiazol-3-yl, indolyl, e.g. indol-4-yl, quinolinyl, e.g. quinolin-2-yl, isoquinolinyl, e.g. isoquinolin-1-yl, 2-oxobenzimidazol-4-yl, naphthyridinyl, e.g. 1,8-naphthyridin-2-yl, or benzofuranyl, for example benzofuran-4-yl or benzofuran-5-yl.

Possible substituents of radicals Ar, for example of the radicals defined in detail above and of the radicals mentioned hereinbefore as examples, are, for example, optionally substituted, especially in the manner specified hereinafter, lower alkyl, lower alkenyl or lower alkoxy, also lower alkenyloxy, lower alkynyl, lower alkynyloxy, cyano and/or nitro, and/or, as substituents bonded directly or to the above-mentioned lower alkyl, lower alkenyl or lower alkoxy, one or more of lower alkanoyl, cycloalkyl, esterified or amidated carboxyl, especially lower alkoxycarbonyl or optionally substituted carbamoyl, for example carbamoyl, lower alkylcarbamoyl, di-lower alkylcarbamoyl or (hydroxy-lower alkyl)carbamoyl, lower alkylsulphinyl, lower alkylsulphonyl, sulphamoyl or lower alkylsulphamoyl; or halogen bonded directly or halogen bonded to the above-mentioned lower alkyl or, in a position higher than the 1-position, halogen bonded to the above-mentioned lower alkoxy; or optionally etherified or esterified hydroxy, such as hydroxy, bonded directly or bonded to the above mentioned lower alkyl such as hydroxy-lower alkyl or polyhydroxy-lower alkyl, substituents not directly bonded are, again, lower alkoxy, cycloalkyl-lower alkoxy, also phenyl-lower alkoxy, or lower alkanoyloxy, etherified mercapto, such as lower alkylthio, optionally substituted amino, such as amino, lower alkylamino, di-lower alkylamino, alkyleneamino or oxaalkyleneamino, pyrrol-1-yl, acylamino, such as lower alkanoylamino, lower alkoxycarbonylamino, optionally substituted ureido, especially ureido substituted by one or two lower alkyl radicals, by hydroxy-lower alkyl or by cycloalkyl, lower alkylsulphonylamino or N-lower alkyl lower alkylsulphonylamino.

The radicals and compounds denoted by "lower" in connection with the present description contain preferably up to 7, and especially up to 4, carbon atoms.

The general terms used in the enumeration of substituents of the radical Ar may have, for example, the following specific meanings. Lower alkyl is, for example, methyl, ethyl, n-propyl, isopropyl, n-butyl, isobutyl, or tert.-butyl; substituted lower alkyl is especially corresponding methyl or 1- or 2-substituted ethyl. Lower alkenyl is, for example, vinyl, allyl, 2- or 3-methallyl or 3,3-dimethallyl, and substituted lower alkenyl is especially 2-substituted vinyl or 3-substituted allyl. Cycloalkyl has from 3 to 7 ring members and is for example, cyclopropyl. Lower alkoxy is, for example, methoxy, ethoxy, n-propoxy, isopropoxy, n-butoxy or isobutoxy, and substituted lower alkoxy is, for example, substituted methoxy or 1- or 2-substituted ethoxy. Lower alkenyloxy is, for example, allyloxy, 2- or 3-methallyloxy or 3,3-dimethallyloxy. Lower alkynyl is, for example, propargyl, and lower alkynyloxy is especially propargyloxy. Lower alkanoyl is, for example, acetyl, propionyl or butyryl. Lower alkoxycarbonyl is, for example, methoxycarbonyl or ethoxycarbonyl. Lower alkylcarbamoyl or di-lower alkylcarbamoyl is, for example, methylcarbamoyl, dimethylcarbamoyl ethylcarbamoyl or diethylcarbamoyl, and hydroxy-lower alkylcarbamoyl is, for example, (2-hydroxyethyl)carbamoyl. Lower alkylsulphinyl is, for example, methyl- or ethylsulphinyl, lower alkylsulphonyl is, for example, methyl-, ethyl- or propylsulphonyl, and lower alkylsulphamoyl is, for example, methyl-, ethyl- or isopropylsulphamoyl. Halogen may be bromine os iodine, but is preferably fluorine or chlorine. Cycloalkyl-lower alkoxy is for example cyclopropylmethoxy or 1- or 2-cyclopropylethoxy. Phenylower alkoxy is, for example, benzyloxy or 1- or 2-phenylethoxy, and lower alkanoyloxy is, for example, formyloxy, acetoxy, propionyloxy, butyryloxy or isobutyryloxy. Lower alkylthio is, for example, methylthio, n-propylthio or isopropylthio. Lower alkylamino and di-lower alkylamino are, for example, methylamino, ethylamino, dimethylamino or diethylamino. Alkyleneamino and oxa-alkyleneamino are, e.g., pyrrolidino, piperidino or morpholino. Lower alkanoylamino is, for example, acetylamino or butyrylamino, and lower alkoxycarbonylamino is, for example, methoxycarbonylamino or ethoxycarbonylamino. Ureido substituted by one or two lower alkyl radicals, by hydroxy-lower alkyl or by cycloalkyl preferably having 5 to 7 ring members, is e.g. 3-methylureido, 3,3-dimethylureido, 3-(2-hydroxyethyl-)ureido, or 3-cyclohexylureido. Lower alkylsulphonylamino is e.g. ethylsulphonylamino and especially methylsulphonylamino, N-lower alkyl lower alkylsulphonylamino is e.g. N-methyl methylsulphonylamino.

As stated above, substituents of Ar may be one of the above-mentioned radicals which is bonded not directly but through lower alkyl, lower alkoxy or optionally also through lower alkenyl. General and specific examples of such substituents are given in the following but the possible combinations are not limited thereto. Lower alkanoylalkyl is e.g. 2-oxopropyl (acetonyl) or 3-oxobutyl; lower alkanoyl-lower alkenyl is e.g. 3-oxobut-1-enyl, and lower alkanoylalkoxy is e.g. 2-oxopropoxy (acetonyloxy) or 3-oxobutoxy. Optionally substituted carbamoyl-lower alkyl is e.g. carbamoylmethyl or [(hydroxy-lower alkyl)carbamoyl)]-lower alkyl, such as [(2-hydroxyethyl)carbamoyl)]methyl. Lower alkoxycarbonyl-lower alkoxy is e.g. ethoxycarbonylmethoxy. Optionally substituted carbamoyl-lower alkoxy is, for example, carbamoyl-lower alkoxy, such as carbamoylmethoxy, or [(hydroxy-lower alkyl)carbamoyl]-lower alkoxy, such as [(2-hydroxyethyl)carbamoyl]methoxy. Halo-lower alkyl is especially halomethyl, e.g. trifluoromethyl. Hydroxy-lower alkyl is preferably hydroxymethyl, or 1- or especially 2-hydroxyethyl. Polyhydroxy-lower alkyl is, for example, di- or trihydroxy-lower alkyl such as 1,2-dihydroxy- or 2,3-dihydroxy-lower alkyl for example 1,2-dihydroxy- or 2,3-dihydroxypropyl. Lower alkoxy-lower alkyl is preferably lower alkoxymethyl or 1- or especially 2-lower alkoxyethyl, e.g. methoxymethyl, ethoxymethyl, 2-methoxyethyl or 2-ethoxyethyl. Cycloalkyl-lower alkoxy-lower alkyl is preferably cycloalkyl-lower alkoxy methyl or 1- or 2-(cycloalkyl-lower alkoxy)-ethyl e.g. 1- or 2-(cyclopropylmethoxy)-ethyl. Lower alkoxy-lower alkoxy is especially 2-lower alkoxyethoxy, such as 2-methoxyethoxy or 2-ethoxyethoxy; lower alkylthio-lower alkoxy is e.g. 2-methylthioethoxy or 2-ethylthioethoxy. Acylamino-lower alkyl is e.g. lower alkanoylamino-lower alkyl, especially lower alkanoylaminomethyl, or 1- or especially 2-lower alkanoylaminoethyl, e.g. acetylaminomethyl, 2-acetylaminoethyl or 2-propionylaminoethyl; or lower alkoxycarbonylamino-lower alkyl, especially lower alkoxycarbonylaminomethyl, or 1- or especially 2-lower alkoxycarbonylaminoethyl e.g. methoxycarbonylaminomethyl, 2-methoxycarbonylaminoethyl or 2-ethoxycarbonylaminoethyl. Acylamino-lower alkoxy is e.g. lower alkanoylamino-lower alkoxy, especially 2-lower alkanoylaminoethoxy, e.g. 2-(acetylamino)ethoxy, or lower alkoxycarbonylamino-lower alkoxy, especially 2-(lower alkoxycarbonylamino)ethoxy, e.g. 2-(methoxycarbonylamino)ethoxy or 2-(ethoxycarbonylamino)ethoxy. Lower alkylcarbamoyl lower alkenyl is, for example, N-methylcarbamoyl lower alkenyl such as N-methylcarbamoyl vinyl.

Alkylene alk may be straight chain or branched and is, for example, ethylene, trimethylene, propylene, tetramethylene, 1-methyltrimethylene, 1,1-dimethyltrimethylene or 1,1-dimethylethylene.

$R_1$ and $R_2$ having the meaning lower alkyl are, for example, propyl, isopropyl, butyl, isobutyl, sec.-butyl, pentyl, isopentyl, neopentyl, hexyl or heptyl, and especially methyl or ethyl. Together with the nitrogen atom of the amide group, $R_1$ and $R_2$ as lower alkylene are, for example, aziridin-1-yl, azetidin-1-yl, pyrrolidino, piperidino, hexahydro-1H-zepin-1-yl; as oxa-lower alkylene e.g. morpholino; as thia-lower alkylene e.g. thiomorpholino; as aza-lower alkylene e.g. piperazin-1-yl or hexahydro-1H-1,4-diazepin-1-yl, wherein the two last-mentioned groups, corresponding to the meaning N-lower alkyl-aza-lower alkylene for $R_1$ and $R_2$ in the 4-position, that is in the imino group, may be substituted, for example, by lower alkyl, such as methyl, ethyl, propyl, isopropyl, butyl or isobutyl.

The phenyl radical carrying the amide and the hydroxy group may be bonded in any position to the remainer of the molecule; preferably, the latter is bonded in the 4-position of the said phenyl radical, that is, in the position para to the amide group, and is bonded especially in the 5-position of the said phenyl radical, (that is, in the position para to the hydroxy group).

The new compounds may exist in the form of their salts, such as their acid addition salts, and especially in the form of their pharmaceutically acceptable, non-toxic acid addition salts. Suitable salts are e.g. those with inorganic acids, such as hydrohalic acids, e.g. hydrochloric acid or hydrobromic acid, sulphuric acid or phosphoric acid, or with organic acids, such as aliphatic, cycloaliphatic, aromatic or heterocyclic carboxylic or sulphonic acids, e.g. formic, acetic, propionic, succinic, glycolic, lactic, malic, tartaric, citric, maleic, hydroxymaleic, pyruvic, fumaric, benzoic, 4-aminobenzoic, anthranilic, 4-hydroxybenzoic, salicylic, embonic, methanesulphonic, ethanesulphonic, 2-hydroxyethanesulphonic, ethylenesulphonic, toluenesulphonic, naphthalenesulphonic or sulphanilic acid, or with other acidic organic substances, such as ascorbic acid.

The new compounds have valuable pharmacological properties. In particular, they act in a specific manner on β-adrenergic receptors. This action is attributed to the affinity for these receptors, which is a property common to the compounds of the formula I. With no or only very slight inherent stimulating action this affinity is reflected as a pure blocking, and with slight to moderate inherent stimulating action is reflected as a blocking with simultaneous ISA (i.e. intrinsic sympathomimetic activity), and, with relatively strong inherent action, as actual stimulation of the β-adrenergic receptors. Pronounced β-receptor-stimulating and at the same time cardioselective activity is found especially with those compounds of formula I in which Ar represents a hydroxyphenyl radical. Of the remaining compounds of the formula I, the β-receptor-blockers with or without ISA, those having a substituent in the p-position, such as especially 1-[2-(3-carbamoyl-4-hydroxyphenoxy)ethylamino]-3-[4-(2-methoxyethoxy)phenoxy]propan-2-ol, exhibit a more or less pronounced cardioselectivity. This action is less clear, or lacking, however, in compounds with ortho-substitution in the broadest sense, that is, the presence of a single substituent or a fused ring in the position ortho to the ether group. On the other hand, such compounds in addition have α-receptor blocking properties. An example of such a compound is especially 1-(2-allyloxyphenoxy)-3-[2-(3-carbamoyl-4-hydroxyphenoxy)ethylamino]propan-2-ol.

The above details referring to pharmacological properties are based on the results of appropriate pharmacological experiments in conventional test methods. Thus, in a concentration range of from approximately 0.001 μg/ml to approximately 1 μg/ml the new β-blocking compounds inhibit tachycardia induced by isoproterenol in isolated guinea pig hearts and in a dosage range of from approximately 0.001 mg/kg to approximately 3 mg/kg, they inhibit the same condition in anaesthetised cats when administered intravenously. In the same dosage range, in anaesthetised cats the β-blocking compounds of the formula I also inhibit an increase in heart rate induced by electrical stimulation of the sympathetic nerves. The inhibition of vasodilation induced by isoproterenol in anaesthetised cats with perfusion of the arteria femoralis can be demonstrated with cardioselective compounds of the formula I when administered intravenously in a dosage range of from approximately 0.1 mg/kg to approximately 30 mg/kg, and with non-cardioselective compounds in a dosage range of from 0.001 to 1 mg/kg. The ISA of the β-blocking compounds of the formula I is shown by the increase in the basal heart rate is anaesthetised cats previously treated with reserpine, when the compounds are administered intravenously in a dosage range of from 0.001 to 1 mg/kg. The new β-blocking compounds also cause a reduction in arterial blood pressure of anaesthetised cats in a dosage range of from approximately 0.01 mg/kg to approximately 10 mg/kg i.v. The additional α-blocking activity of the non-cardioselective β-receptor-blockers which may, for example, promote a blood pressure-reducing action, is shown, for example, in the antagonisation of the noradrenalin-induced contraction of the isolated vas deferens of rats by such compounds in a concentration of from 0.01–3 μg/ml. The new β-blocking compounds of the formula I may be used as optionally cardioselective β-receptor-blockers, for example for the treatment of angina pectoris and cardiac arrthythmia, and as blood pressure-inducing agents.

The β-stimulating compounds of the formula I, such as 1-(4-hydroxyphenoxy)-3-[2-(3-carbamoyl-4-hydroxyphenoxy)-1-methylethylamino]propan-2-ol, for example that racemate of which the neutral fumarate melts at 195°–198°, cause an increase in heart rate and myocardial contraction force in the isolated guinea pig auricle in a concentration range of from approximately 0.001 to 0.1 μg/ml, and cause an increase in heart rate and maximum pressure increase speed in the left ventricle (dp/dt max), in anaesthetised cats in a dosage range of from approximately 0.0001 to approximately 0.1 mg/kg i.v. On the other hand, higher doses, corresponding to a dosage range of from approximately 0.001 to approximately 1 mg/kg i.v., are required to reduce arterial blood pressure in anaesthetised cats, that is to say, the new compounds stimulate specifically the cardial β-receptors (β1-receptors) compared with the β-receptors in the blood vessels (β2-receptors) and are thereby qualitatively clearly distinguished from isoproterenol which stimulates the β-receptors of the heart and the blood vessels approximately equally strongly. The new compounds may therefore be used as positively inotropically acting agents, especially as cardiotonic agents for the treatment of myocardial insufficiency, either alone or in combination with other preparations, such as cardiac glycosides, and also for the treatment of certain disturbances in cardiac rhythm.

Compounds of the formula I, in which Ar is phenyl unsubstituted or substituted one to three times by hydroxy exhibit effects on the central nervous system, which are reflected for example in the suppression of the symptoms of impaired sympathetic functions and in the suppression of lack of initiative, as can be demonstrated for example by virtue of the antagonism against hypothemia induced in mice after s.c.-administration of 2 mg/kg of reserpine (B. Benz et al; Arzneimittelforschung 21, 654–61 (1971)) in a dose of about 3 mg/kg to about 100 mg/kg i.p., or by virtue of the antagonism against hypothemia induced in mice after s.c.-administration of 10 mg/kg of apomorphine (Puech A. L.; Europ. J. of Pharmacol. 47, 127–27 (1978); Schelkunov E. L.: Psychopharmacol. 55, 87–95 (1977)) in a dose range of about 0.03 mg/kg to about 1 mg/kg i.p., or by virtue of the antagonism against hypothemia induced in mice after i.p.-administration of 0.25 mg/kg of clonidine (Voigtlaender P. F. et al; Neuropharmacol. 17, 375–81 (1978)) in a dose range of about 0.01 mg/kg to about 0.3 mg/kg i.p. With respect to these results such compounds of the formula I can be used for the treatment of reactive or endogenic states of depression of varying degrees of severity, and also for the treatment of neurotic or other psychic disturbances involving loss of initiative and depressive disorders. Such compounds can also be used for the short-term treatment of postpartum or postoperative depression, or of depression of different origin. Such compounds of the formula I can be used on their own or in combination with other antidepressants.

The compounds of the general formula I may also be used as valuable intermediates for the preparation of other more valuable compounds, especially compounds that are pharmaceutically more effective.

The invention relates in particular to compounds of the formula I in which Ar represents monocyclic or bicyclic carbocyclic aryl or monocyclic or bicyclic heteroaryl bonded by a ring carbon atom and containing as ring members a maximum of two nitrogen atoms and/or one oxygen or sulphur atom, which radicals may be unsubstituted or substituted one or more times, preferably at most three times, wherein as substituents there may be present optionally substituted, especially in the manner specified hereinafter, lower alkyl, lower alkenyl or lower alkoxy, also lower alkenyloxy, lower alkynyl, lower alkynyloxy, cyano and/or nitro, and/or, as substituents bonded directly or to the above-mentioned lower alkyl, lower alkenyl or lower alkoxy, one or more of lower alkanoyl, cycloalkyl, esterified or amidated carboxyl, especially lower alkoxycarbonyl, carbamoyl, lower alkylcarbamoyl or (hydroxy-lower alkyl)carbamoyl, lower alkylsulphinyl, lower alkylsulphonyl, sulphamoyl or lower alkylsulphamoyl; and/or, halogen bonded directly or halogen bonded to the above-mentioned lower alkyl or, in a position higher than the 1-position, halogen bonded to the above-mentioned lower alkoxy; optionally etherified or esterified hydroxy, such as hydroxy bonded directly or bonded to the above-mentioned lower alkyl or, as substituent not directly bonded, again lower alkoxy, cycloalkyl-lower alkoxy, also phenyl-lower alkoxy, for example benzyloxy, or lower alkenyloxy, etherified mercapto, such as lower alkylthio, optionally substituted amino, such as amino, lower alkylamino, di-lower alkylamino, alkyleneamino or oxaalkyleneamino, for example, pyrrolidino, piperidino or morpholino, pyrrol-1-yl, acylamino, such as lower alkanoylamino, lower alkoxycarbonylamino, ureido optionallyl substituted by lower alkyl, by hydroxy-lower alkyl or by cycloalkyl, lower alkylsulphonylamino or N-lower alkyl lower alkylsulphonylamino, and in bicyclic radicals Ar, the ring not directly bonded to the ether group is also at least partially hydrogenated and in this case may also be substituted by oxo; and in which $\underline{n}$ is the number 0 or 1, $\underline{alk}$ is an alkylene radical having from 2 to 4 carbon atoms, the nitrogen atom and the oxygen atom or, if n is 0, the phenyl radical, being separated from one another by 2 or 3 carbon atoms, and $R_1$ and $R_2$ have the meanings given under formula I but preferably represent hydrogen or lower alkyl, for example methyl or ethyl, or together with the nitrogen atom of the amide group, form morpholino or alkyleneamino having 5 or 6 ring members, such as pyrrolidino or piperidino; and salts thereof, especially acid addition salts, more especially pharmaceutically acceptable non-toxic acid addition salts.

The invention relates preferably to compounds of the formula I in which Ar represents monocyclic or bicyclic carbocyclic aryl or monocyclic or bicyclic heteroaryl bonded by a ring carbon atom and containing as ring members a maximum of two nitrogen atoms and/or one oxygen or sulphur atom, which radicals may be unsubstituted or substituted one to three times, wherein as substituents there may be present, optionally substituted in the manner specified hereinafter, lower alkyl, lower alkenyl or lower alkoxy, also lower alkenyloxy, lower alkynyl, lower alkynyloxy, cyano and/or nitro, and/or, as substituents bonded directly or to the above-mentioned lower alkyl, lower alkenyl or lower alkoxy, one or more of lower alkanoyl, cycloalkyl, lower alkoxycarbonyl, carbamoyl, lower alkylcarbamoyl or (hydroxy-lower alkyl)-carbamoyl, lower alkylsulphinyl, lower alkylsulphonyl, sulphamoyl or lower alkylsulphamoyl; and/or halogen bonded directly or halogen bonded to the above-mentioned lower alkyl or, in a position higher than the 1-position, halogen bonded to the above-mentioned lower alkoxy; hydroxy, hydroxy-lower alkyl or polyhydroxy-lower alkyl, or, as substituent not directly bonded, again lower alkoxy, cycloalkyl-lower alkoxy, phenyl-lower alkoxy, for example benzyloxy, lower alkanoyloxy, lower alkylthio, amino, lower alkylamino, di-lower alkylamino, alkyleneamino or oxaalkyleneamino, for example pyrrolidino, piperidino or morpholino, pyrrol-1-yl, lower alkanoylamino or lower alkoxycarbonylamino, ureido optionlly substituted by lower alkyl, by hydroxy-lower alkyl or by cycloalkyl, lower alkylsulphonylamino or N-lower alkyl lower alkylsulphonylamino, and, in bicyclic radicals Ar, the ring not directly bonded to the ether group is also at least partially hydrogenated and in this case may also be substituted by oxo; and in which $\underline{n}$ represents the number 0 or 1, $\underline{alk}$ represents an alkyene radical having from 2 to 4 carbon atoms, the nitrogen atom and the oxygen atom or, if n is 0, the phenyl radical, being separated from one another by 2 or 3 carbon atoms, and $R_1$ and $R_2$ have the meanings given under formula I but preferably represent hydrogen or lower alkyl, especially methyl or ethyl, or, together with the nitrogen atom of the amide group, form pyrrolidino, piperidino or morpholino; and salts thereof, especially acid addition salts, more especially pharmaceutically acceptable, non-toxic acid addition salts.

The invention relates especially to compounds of the formula I in which Ar represents phenyl, naphthyl or 1,2,3,4-tetrahydro-5-naphthyl, which radicals may be unsubstituted or substituted one to three times, wherein as substituents there may be present, optionally substituted in the manner specified hereinafter, lower alkyl, lower alkenyl or lower alkoxy, also lower alkenyloxy, lower alkynyloxy, and/or cyano, and/or, as substituents bonded directly or to the above-mentioned lower alkyl, lower alkenyl or lower alkoxy, one or more of lower alkanoyl, lower alkoxycarbonyl, cycloalkyl, carbamoyl, lower alkylcarbamoyl or (hydroxy-lower alkyl)carbamoyl, lower alkylsulphinyl, lower alkylsulphonyl, sulphamoyl or lower alkylsulphamoyl; and/or halogen bonded directly or halogen bonded to the above-mentioned lower alkyl or, in a position higher than the 1-position, halogen bonded to the above-mentioned lower alkoxy; hydroxy, hydroxy-lower alkyl or polyhydroxylower alkyl, or, as substituent not directly bonded, again lower alkoxy, cycloalkyl-lower alkoxy, also phenoxy-lower alkoxy, for example benzyloxy, lower alkanoyloxy, lower alkylthio, amino, lower alkylamino, di-lower alkylamino, alkyleneamino or oxaalkyleneamino, for example pyrrolidino, piperidino or morpholino, pyrrol-1-yl, lower alkanoylamino or lower alkoxycarbonylamino, ureido optionally substituted by lower alkyl or cycloalkyl, lower alkylsulphonylamino or N-lower alkyl lower alkylsulphonylamino, and in which $\underline{n}$ represents the number 0 or 1, $\underline{alk}$ represents an alkylene radical having from 2 to 4 carbon atoms, the nitrogen atom and the oxygen atom or, if $\underline{n}$ is 0, the phenyl radical, being separated from one other by 2 or 3 carbon atoms, and $R_1$ and $R_2$, independently of one another, each represents hydrogen or lower alkyl, especially methyl or ethyl, or, together with the nitrogen atom of the amide group, form morpholino; and salts thereof, especially acid addition salts, more especially pharmaceutically acceptable non-toxic acid addition salts.

The invention relates especially to compounds of the formula I in which Ar represents phenyl which may be unsubstituted or substituted one to three times, wherein as substituents there may be present, optionally substituted in the manner specified hereinafter, lower alkyl or lower alkoxy, also lower alkenyl, lower alkenyloxy, lower alkynyloxy, and/or cyano, and/or, as substituents bonded directly or to the above-mentioned lower alkyl, lower alkoxy or lower alkenyl, one or more of lower alkanoyl, cycloalkyl, lower alkoxycarbonyl, carbamoyl, lower alkylcarbamoyl or (hydroxy-lower alkyl)carbamoyl, lower alkylsulphinyl or lower alkylsulphonyl; and/or halogen bonded directly or halogen bonded to the above-mentioned lower alkyl or, in a position higher than the 1-position halogen bonded to the above-mentioned lower alkoxy; hydroxy, hydroxy-lower alkyl or polyhydroxy-lower alkyl, or, as substituent not directly bonded, again lower alkoxy, cycloalkyl-lower alkoxy, also phenyl-lower alkoxy, for example benzyloxy, lower alkylthio, alkyleneamino, or oxaalkyleneamino, for example pyrrolidino, piperidino or morpholino, pyrrol-1-yl, lower alkanoylamino or lower alkoxycarbonylamino, or ureido optionally substituted by lower alkyl, lower alkylsulphonylamino or N-lower alkyl lower alkylsulphonylamino; and in which $\underline{n}$ represents the number 0 or 1, $\underline{alk}$ represents an alkylene radical having from 2 to 4 carbon atoms, the nitrogen atom and the oxygen atom or, if $\underline{n}$ is 0, the phenyl radical, being separated from one another by 2 or 3 carbon atoms, and $R_1$ and $R_2$ independently of one another each represents hydrogen or lower alkyl, but preferably hydrogen or methyl; and salts thereof, especially acid addition salts, more especially pharmaceutically acceptable non-toxic acid addition salts.

The invention relates especially to compounds of the formula I in which Ar represents phenyl which may be unsubstituted or substituted one to three times, wherein as substituents there may be present, optionally substituted in the manner specified hereinafter, lower alkyl or lower alkoxy, also lower alkenyl, lower alkenyloxy, lower alkynyloxy, and/or cyano, and/or as substituents bonded directly or to the above-mentioned lower alkyl, lower alkoxy or lower alkenyl, one or more of lower alkanoyl, cycloalkyl, carbamoyl, lower alkylcarbamoyl or (hydroxy-lower alkyl)-carbamoyl, lower alkylsulphinyl and lower alkylsulphonyl; and/or fluorine or chlorine bonded directly or to the above-mentioned lower alkyl or, in a position higher than the 1-position, to the above-mentioned lower alkoxy; hydroxy, hydroxy-lower alkyl or 1,2,-dihydroxy- or 2,3,-dihydroxy-lower alkyl, such as 2,3-dihydroxypropyl, or, as substituent not directly bonded, again lower alkoxy, cycloalkyl-lower alkoxy such as cyclopropylmethoxy, also phenyl-lower alkoxy, for example benzyloxy, lower alkylthio, pyrrol-1-yl, lower alkanoylamino, lower alkoxycarbonylamino, ureido, lower alkylsulphonylamino such as methylsulphonylamino, N-lower alkyl lower alkylsulphonylamino such as N-methyl methylsulphonylamino; and in which $\underline{n}$ represents the integer 1, $\underline{alk}$ represents an alkylene radical having from 2 to 4 carbon atoms, the nitrogen atom and the oxygen atom being separated from one another by 2 carbon atoms, and $R_1$ and $R_2$ represent hydrogen, and the phenyl radical carrying the amide and the hydroxy group is bonded preferably in its 4-position, and especially in its 5-position, to the remainder of the molecule; and salts thereof, especially acid addition salts, more especially pharmaceutically acceptable nontoxic acid addition salts.

The invention relates especially to compounds of the formula I in which Ar represents phenyl unsubstituted or substituted one or three times by hydroxy, $\underline{n}$ represents the integer 1, e,uns/alk/ represents an alkylene radical having from 2 to 4 carbon atoms, the nitrogen atom and the oxygen atom being separated from one another by 2 carbon atoms, $R_1$ and $R_2$ represent hydrogen or lower alkyl, such as methyl, and the phenyl radical carrying the amide and the hydroxy group is bonded preferably in its 4-position, and especially in its 5-position to the remainder of the molecule, and salts thereof, especially acid addition salts, more especially pharmaceutically acceptable nontoxic acid addition salts.

The new compounds of the formula I are prepared in a manner known per se. They may be obtained, for example by reacting a compound of the formula $$Ar-O-CH_2-\overset{X_1}{\underset{|}{CH}}-CH_2-Z_1 \qquad (II)$$

with a compound of the formula

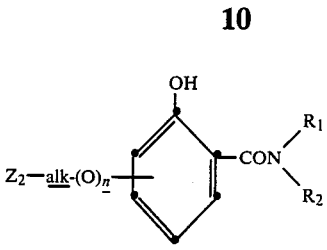

in which
one of the groups $Z_1$ and $Z_2$ represents a reactive esterified hydroxy group and the other represents the primary amino group, and
$X_1$ represents hydroxy,
or in which
$X_1$ and $Z_1$ together represent the epoxy group and
$Z_2$ represents the primary amino group,
and Ar, $\underline{n}$, $\underline{alk}$, $R_1$ and $R_2$ have the meanings given above, and, if desired, converting a compound which may be thus obtained into a different compound of the formula I and/or if desired, converting a resulting free compound into a salt or a resulting salt into a free compound and/or, if desired, separating a resulting isomeric mixture into its isomers or a resulting racemate into its antipodes.

A reactive esterified hydroxy group $Z_1$ or $Z_2$ is a hydroxy group esterified by a strong acid, especially a strong inorganic acid, such as a hydrohalic acid, especially hydrochloric, hydrobromic or hydriodic acid, or sulphuric acid, or by a strong organic acid, especially a strong organic sulphonic acid, such as an aliphatic or aromatic sulphonic acid, for example methanesulphonic acid, 4-methylphenylsulphonic acid or 4-bromophenylsulphonic acid, and is especially halogen, for example chlorine, bromine or iodine, or aliphatically or aromatically substituted sulphonyloxy, for example methylsulphonyloxy or 4-methylphenylsulphonyloxy.

The above reaction is carried out in a manner known per se, wherein, especially when using a starting material having a reactive esterified hydroxy group, the reaction is carried out advantageously in the presence of a basic medium, such as an inorganic base, for example an alkali metal or alkaline earth metal carbonate or hydroxide, or in the presence of an organic basic medium, such as an alkali metal lower alkanolate, and/or an excess of the basic reactant, and usually in the presence of a solvent or mixture of solvents, and, if necessary, whilst cooling or heating for example in a temperature range of from approximately $-20°$ C. to approximately $150°$ C., in an open or closed vessel and/or in an inert gas atmosphere, for example a nitrogen atmosphere.

Starting materials of the formula II are known or can be prepared in a manner known per se.

Starting materials of the formula III may be obtained, for example, by reacting a hydroxysalicylic amide with a dihaloalkane corresponding to the meaning of $\underline{alk}$, for instance a chloro-bromoalkane or dibromoalkane, in the presence of an alkaline condensing agent, such as an alkali metal carbonate. These reactions are carried out in the customary manner, protecting groups at the hydroxy groups being simultaneously or, as described hereinafter, subsequently split off.

The compounds of the formula I may also be prepared by a process which is characterised in that in a compound of the formula

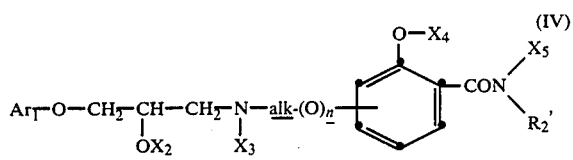

in which
- Ar$_1$ has the same meaning as Ar or represents a radical Ar that is substituted by 1 or 2 groups that may be converted into hydroxy,
- X$_2$, X$_3$ and X$_4$ each represents hydrogen or a substituent that may be replaced by hydrogen, and
- X$_5$ represents R$_1$, or
- X$_2$ and X$_3$ and/or
- X$_4$ and X$_5$ together represent a divalent radical that may be replaced by two hydrogen atoms, provided that at least one of the radicals X$_2$, X$_3$ and X$_4$ is different from hydrogen, or at least Ar$_1$ represents a radical Ar that is substituted by 1 or 2 groups that may be converted into hydroxy, or at least X$_2$ and X$_3$ together or X$_4$ and X$_5$ together represent a divalent radical that may be replaced by two hydrogen atoms, or in a salt of the compound of the formula (IV) those of the groups X$_2$, X$_3$ and X$_4$, or X$_2$ and X$_3$ together, or X$_4$ and X$_5$ together, which are other than hydrogen are replaced by hydrogen atoms, and/or substituted hydroxy present in a radical Ar$_1$ is converted into free hydroxy and, if desired, the additional process steps following the first process are subsequently carried out.

The splitting off of the groups X$_2$, X$_3$ or X$_4$ X$_2$ and X$_3$ together or X$_4$ and X$_5$ together, and of the hydroxy substituents present in a radical Ar$_1$ is effected by solvolysis for example by hydrolysis, alcoholysis, or by reduction including hydrogenolysis.

An especially suitable group X$_3$ or X$_4$ that is capable of being split off, or a hydroxy-protecting group in a radical Ar$_1$ is especially a α-aryl-lower alkyl group that is capable of being split off by hydrogenolysis, such as an optionally substituted 1-polyphenyl-lower alkyl group or 1-phenyl-lower alkyl group, in which substituents, especially of the phenyl moiety, may be, for example, lower alkyl, such as methyl, or lower alkoxy, such as methoxy, and especially benzyl. A group X$_3$ and especially X$_2$ and X$_4$ and also hydroxy-protecting groups in a radical Ar$_1$ may also be radicals capable of being split off by solvolysis, such as by hydrolysis or acidolysis, or radicals capable of being split off by reduction, including hydrogenolysis, especially a corresponding acyl radical, such as the acyl radical of an organic carboxylic acid, for example lower alkanoyl, such as acetyl, or aroyl, such as benzoyl, the acyl radical of a semi-ester of carbonic acid, such as lower alkoxycarbonyl, for example methoxycarbonyl, ethoxycarbonyl, or tert.-butoxycarbonyl, 2-halo-lower alkoxycarbonyl, for example 2,2,2-trichloroethoxycarbonyl or 2-iodoethoxycarbonyl, optionally substituted 1-phenyl-lower alkoxycarbonyl, for example benzyloxycarbonyl or diphenylmethoxycarbonyl, or aroylmethoxycarbonyl, for example phenacyloxycarbonyl, or an optionally substituted 1-polyphenyl-lower alkyl group, in which substituents, especially of the phenyl moiety, for example have the meaning given above, and represent especially trityl.

A radical capable of being split off and formed by X$_2$ and X$_3$ and/or X$_4$ and X$_5$ together, is especially a group that can be split off by hydrogenolysis, such as optionally substituted 1-phenyl-lower alkylidene, in which substituents, especially of the phenyl moiety, may be, for example, lower alkyl or lower alkoxy, and especially benzylidene, and also groups that can be split off by solvolysis, especially by hydrolysis, such as lower alkylidene, for example methylene or isopropylidene, or 1-phenyl-lower alkylidene of which the phenyl moiety is optionally substituted by lower alkyl, such as methyl, or lower alkoxy, such as methoxy, especially benzylidene, or cycloalkylidene, for example cyclopentylidene or cyclohexylidene.

Starting materials that may be used in the form of salts are used especially in the form of acid addition salts, for example with mineral acids, and with organic acids.

Radicals X$_2$, X$_3$ and/or X$_4$ that can be split off by hydrogenolysis, especially optionally substituted 1-phenyl-lower alkyl groups, also suitable acyl groups, such as optionally substituted 1-phenyl-lower alkoxycarbonyl, and optionally substituted 1-phenyl-lower alkylidene groups formed by the groups X$_2$ and X$_3$ and by X$_4$ and X$_5$ together, and also hydroxy-protecting groups of this kind present in a radical Ar$_1$, can be split off by treating with catalytically activated hydrogen, for example hydrogen in the presence of a nickel catalyst, such as Raney nickel, or a suitable noble metal catalyst.

Groups X$_2$, X$_3$ and/or X$_4$ that can be split off by hydrolysis, such as acyl radicals of organic carboxylic acids, for example lower alkanoyl, and of semi-esters of carbonic acid, for example lower alkoxycarbonyl, also for example trityl radicals, and also lower alkylidene, 1-phenyl-lower alkylidene or cycloalkylidene groups formed by the radicals X$_2$ and X$_3$ and/or X$_4$ and X$_5$ together, and also hydroxy-protecting groups of this kind present in a radical Ar$_1$, may, depending on the nature of such radicals, be split off by treating with water under acidic or basic conditions, for example in the presence of a mineral acid, such as hydrochloric acid or sulphuric acid, or an alkali metal or alkaline earth metal hydroxide or carbonate, or an amine, such as isopropylamine.

Radicals X$_2$, X$_3$ and/or X$_4$ and/or hydroxy-protecting groups in a radical Ar$_1$ that can be split off by acidolysis are especially certain acyl radicals of semi-esters of carbonic acid, such as, for example, tert.-lower alkoxycarbonyl or optionally substituted diphenylmethoxycarbonyl radicals, and the tert.-lower alkyl radical; such radicals can be split off by treating with suitable strong organic carboxylic acids, such as lower alkanecarboxylic acids optionally substituted by halogen, especially fluorine, or especially with trifluoroacetic acid (if necessary in the presence of an activating agent, such as anisole), and with formic acid.

Radicals X$_2$, X$_3$ and/or X$_4$ and/or hydroxy-protecting groups in a radical Ar$_1$ that can be split off by reduction shall also include those groups which are split off when treated with a chemical reducing agent (especially with a reducing metal or a reducing metal compound). Such radicals are, in particular, 2halo-lower alkoxycarbonyl or arylmethoxycarbonyl, which can be split off, for example, by treating with a reducing heavy metal such as zinc, or with a reducing heavy metal salt, such as a chromium(II) salt, for example chromium chloride or acetate, usually in the presence of an organic carboxylic acid, such as formic acid or acetic acid, and water.

Protecting groups positioned at the hydroxy groups optionally present in a radical $Ar_1$ correspond to the previously mentioned groups that can be split off by means of the described methods and replaced by hydrogen, such groups being split off in the course of the described process at the same time as other groups or subsequently in a separate process step.

The above reactions are usually carried out in the presence of a solvent, or a mixture of solvents, wherein suitable reactants may also act simultaneously as such, and, if necessary, whilst cooling or heating, for example in an open or closed vessel, and/or in the atmosphere of an inert gas, for example nitrogen.

The starting material of the formula IV can be obtained analogously to the above described process modifications, for example by treating a compound of the formula $Ar_1OH$ or a salt thereof with a compound of the formula

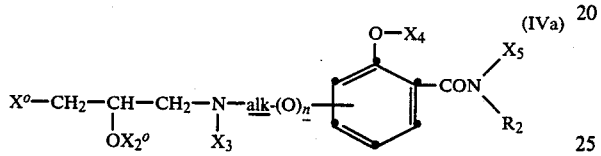 (IVa)

in which $X_2^o$ represents the group $X_2$, wherein at least one of the groups $X_3$ and $X_2^o$ does not represent hydrogen, and $X^o$ represents a reactive esterified hydroxy group, or $X_2^o$ and $X^o$ together represent a carbon-oxygen bond, or in which $X_3$ and $X_2^o$ together represent a radical that is capable of being split off and can be replaced by two hydrogen atoms bonded to the oxygen or nitrogen atom, and $X^o$ represents a reactive esterified hydroxy group, or by treating a compound of the formula

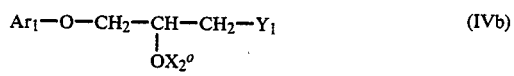 (IVb)

with a compound of the formula

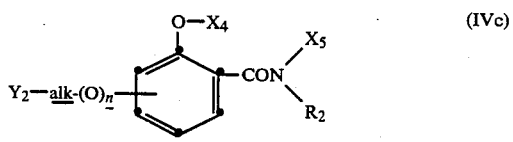 (IVc)

in which $X_2^o$ has the meaning given above for $X_2$, and one of the groups $Y_1$ and $Y_2$ represents a reactive esterified hydroxy group and the other represents the group of the formula $-NH(X_3)$, in which $X_3$ has the meaning given above, provided that at least one of the groups $X_3$ and $X_2$ does not represent hydrogen, or in which $X_2^o$ and $Y_1$ form an oxygen-carbon bond and $Y_2$ represents the group of the formula $-NE(X_3)$ and $X_3$ does not represent hydrogen.

The above reactions are carried out in a manner known per se, for example as described under the first process according to the invention.

Furthermore, the Schiff's base formed by reacting a compound of the formula

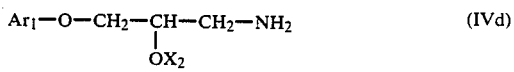 (IVd)

with a carbonyl compound of the formula

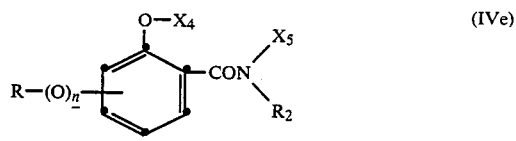 (IVe)

in which

R represents an alkyl radical corresponding to the alkylene radical alk and containing a carbonyl grouping that is separated from the oxygen atom or phenyl radical by at least one carbon atom, and $X_4$ or $X_4$ and $X_5$ together represent one of the mentioned protecting groups, may be reduced, for example, with a borohydride, for instance sodium borohydride, to the compound of the formula IV. The reduction can also be carried out by means of activated hydrogen in the presence of a hydrogenating catalyst, for example a platinum-on-carbon catalyst.

Carbonyl compounds of the formula (IVe) in which n is 1, may in turn be obtained in the customary manner by reacting a compound of the formula

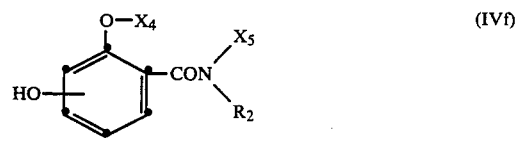 (IVf)

with a compound of the formula R—Hal (Iva) in which R has the meaning given above, for example a haloketone, for example chloroacetone.

The new compounds of the formula I may likewise be obtained by a process which is characterised in that, in a compound of the formula

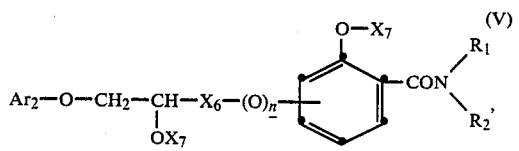 (V)

in which $X_6$ is a reducible group of the formula

 (Va)

or

 (Vb)

in which $alk_1$ represents an alkylylidene radical corresponding to the radical alk, and

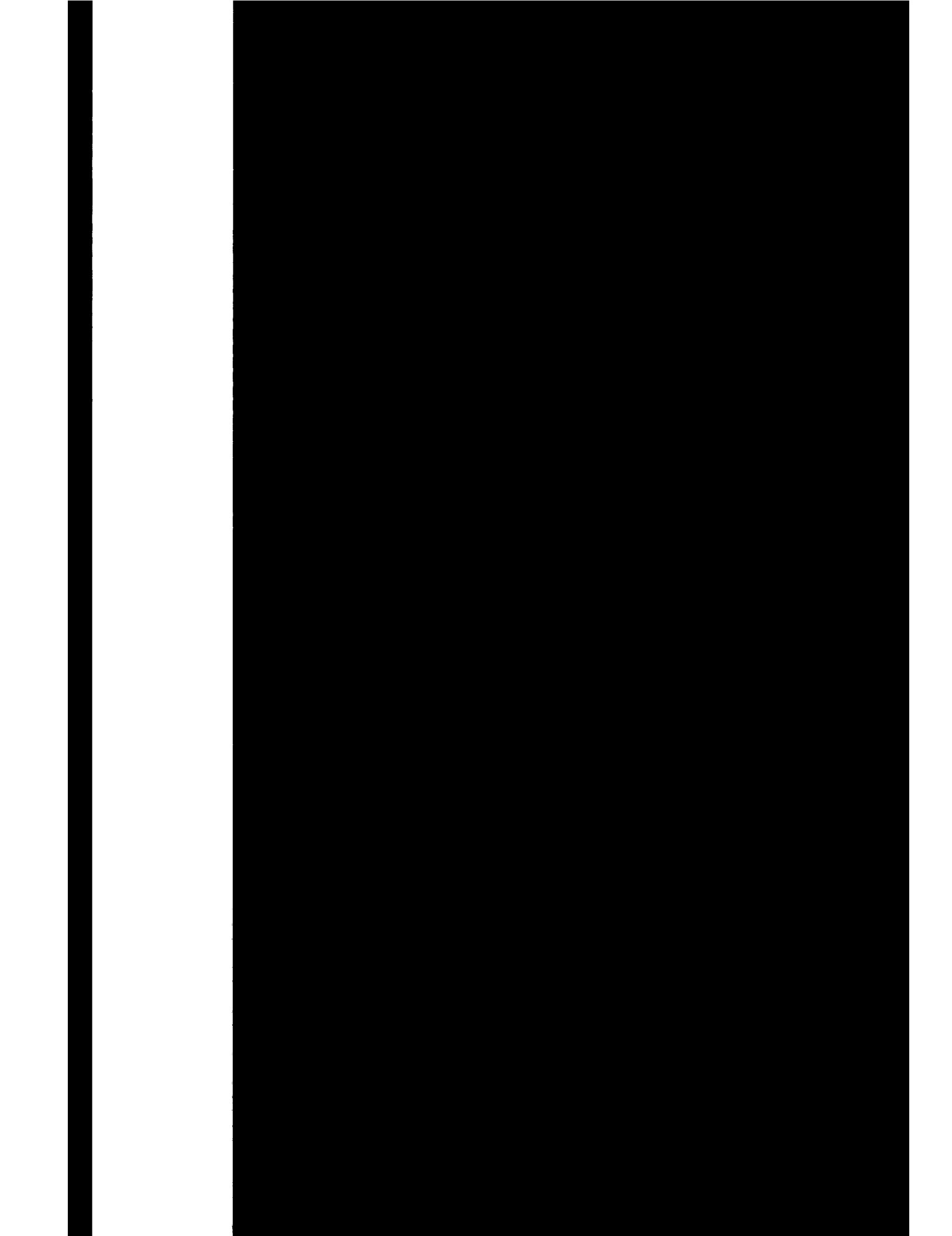

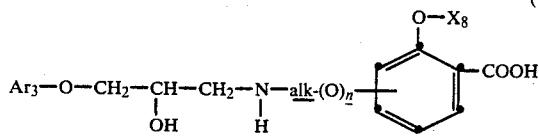 (VI)

in which
Ar₃ has the same meaning as Ar, or represents a radical Ar that is substituted by 1 or 2 groups that may be converted into hydroxy by aminolysis,
X₈ represents hydrogen or a group that can be split off by aminolysis,
or a reactive derivative of one of the carboxylic acids defined in formula VI, with a compound of the formula

HNR₁R₂     (VII)

and at the same time splitting off optionally present X₈ radicals and replacing them by hydrogen, and, if desired, carrying out the additional process steps mentioned following the first process.

X₈ radicals that can be split off by aminolysis and especially by ammonolysis are acyl radicals of organic carboxylic acids, e.g. aroyl, such as benzoyl, or lower alkanoyl, such as acetyl.

Reactive derivatives of the carboxylic acids defined in formula VI are, for example, the halides, such as the chlorides or bromides, the azides, and also acid anhydrides, especially mixed acid anhydrides with, for example, lower alkanecarboxylic acids, such as acetic acid or propionic acid, or lower alkoxyalkanecarboxylic acids, such as 2-methoxyacetic acid. Reactive derivatives of carboxylic acids of the formula VI are especially esters, for example with lower alkanols, such as methanol, ethanol, isopropanol or tert.-butanol, also with aryl lower alkanols, for instance benzyl alcohol optionally substituted by lower alkyl, for example methyl, or lower alkoxy, for example methoxy, or with phenols which are optionally activated by suitable substituents, for example by halogen, for instance 4-halo, such as 4-chloro; lower alkoxy, for instance 4-lower alkoxy, such as 4-methoxy; 4-nitro; or 2,4-dinitro; for instance 4-chlorophenol, 4-methoxyphenol, 4-nitrophenol or 2,4-dinitrophenol; furthermore with cycloalkanols such as cyclopentanol or cyclohexanol, which may optionally be substituted by lower alkyl, for example methyl. The reaction is carried out in a manner known per se, usually in the presence of an inert solvent, for example in a temperature range of from approximately −10° to 50° C. in a closed vessel.

The starting substances of the formula VI may be obtained in a manner known per se by reacting a compound of the formula (II), in which X₁ and Z₁ together represent the epoxy group, with an amino compound of the formula

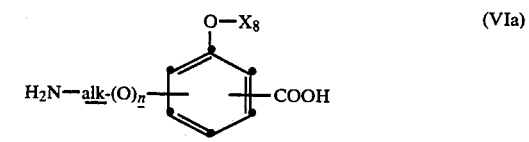 (VIa)

in which X₈ has the meaning given, or with a reactive derivative thereof.

The Schiff's base formed by reacting a compound of the formula

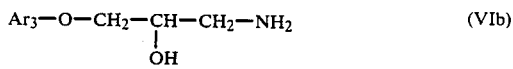 (VIb)

with a carbonyl compound of the formula

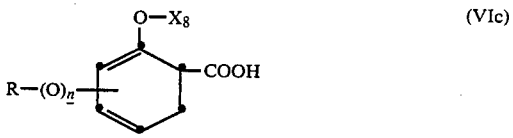 (VIc)

in which
R represents the alkyl radical corresponding to an alkylene radical alk and containing an oxo radical in place of the free valency thereof,
may also be reduced with a borohydride, for instance sodium borohydride. The reduction can also be carried out by means of activated hydrogen in the presence of a hydrogenating catalyst, for example a platinum-on-carbon catalyst.

Carbonyl compounds of the formula (VIc), in which n is 1, may in turn be obtained in a manner known per se by reacting a compound of the formula

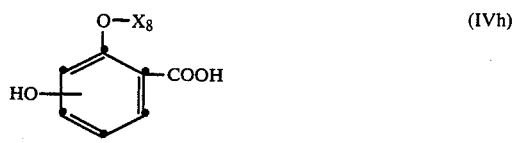 (IVh)

with a compound of the formula

R—Hal     (IVg)

in which Hal represents halogen, especially chlorine.

The new compounds of the formula I may likewise be obtained by a process which is characterised in that, in a compound of the formula

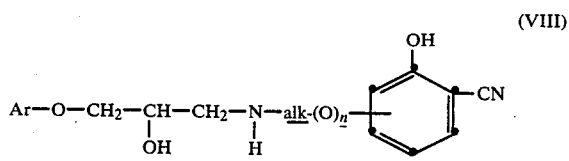 (VIII)

in which one or both hydroxy groups and/or hydroxy groups optionally present in the radical Ar are protected by those groups that can be split off by hydrolysis and replaced by hydrogen, which are split off under the conditions of the process and are replaced by hydrogen,
the —CN group is converted by hydrolysis into the —CONH₂ group and, at the same time, optionally protected hydroxy groups are converted into free hydroxy groups, and, if desired, the additional process steps following the first process are carried out.

The above reactions are carried out in a manner known per se. The hydrolysis is effected in a basic, or, advantageously, in an acidic medium, especially in the presence of concentrated aqueous mineral acids, such as, for example, concentrated hydrochloric acid, and, if necessary, whilst cooling or heating, for example in a temperature range of from approximately 0° to 60°, preferably from approximately 40°–50°, in an open or closed vessel and/or in an inert gas atmosphere, for example in a nitrogen atmosphere.

The starting substances of the formula VIII may be obtained, for example, by reacting a compound of the formula

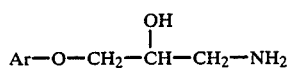 (VIIIa)

with a compound of the formula

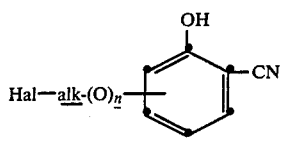 (VIIIb)

in which Hal represents chlorine, bromine or iodine. The reaction is advantageously carried out in the presence of a basic medium in a manner known per se.

The compound VIIIb may in turn be obtained by the action of acetic anhydride on the oxime corresponding to the cyanide. This is expediently carried out by refluxing. The oxime may in its turn be prepared from the corresponding aldehyde by refluxing with hydroxylamine hydrochloride in the presence of alcoholic soda solution. The corresponding aldehyde may in turn be prepared by reacting 2,4-dihydroxybenzaldehyde with a α,ω-dihalolower alkane, preferably in the presence of a basic medium. Alternatively, however, a hydroxysalicylonitrile, for example 2,4-dihydroxybenzonitrile [Chem. Ber. 24, 3657 (1891)] or 2,5-dihydroxybenzonitrile [Helv. Chim. Acta 30, 149, 153 (1947)] may be reacted in an analogous manner with a non-geminal dihalo-lower alkane to form a compound of the formula VIIIb.

The new compounds of the formula I wherein Ar is substituted by hydroxy-lower alkyl or by polyhydroxy-lower alkyl, for example 1,2-dihydroxy- or 2,3-dihydroxy-lower alkyl, such as 1,2-dihydroxy- or 2,3-dihydroxypropyl, can be obtained by a process which is characterised in that in a compound of the formula

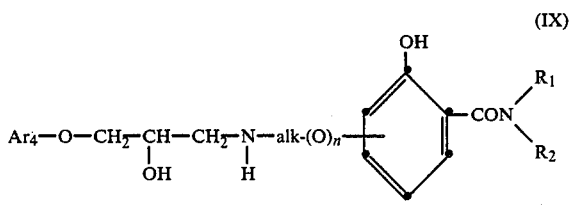 (IX)

wherein Ar4 represents a radical Ar which is substituted by a hydroxy-lower alkyl group of which the hydroxy group is substituted by a radical that can be split off and replaced by hydrogen, or is substituted by a polyhydroxylower alkyl group, for example by one of those mentioned, whereby at least one hydroxy group, or two hydroxy groups together, each of which is located at one of two adjacent hydrocarbon atoms, is (are) protected by a radical that can be split off and replaced by hydrogen, or in a salt thereof, these protecting groups, which can be identical or different, as well as optionally further protecting groups located at the nitrogen atom and/or at the oxygen atoms, are split off, and replaced by hydrogen, and, if desired, the additional process steps described subsequent to the first process are then carried out. Groups which can be split off, and replaced by hydrogen, for example groups that can be split off by means of solvolysis, such as hydrolysis, alcoholysis or acidolysis, or by means of reduction, including hydrogenolysis, for instance as described above, are for example the radicals $X_2$ or $X_4$ described above. Radicals $X_2$ or $X_4$ that can be split off by solvolysis, such as by hydrolysis or acidolysis, are for example acyl radicals, such as acyl radicals of organic carboxylic acids, for example lower alkanoyl, such as acetyl, or aroyl, such as benzoyl, also for example lower-alkoxy carbonyl, optionally substituted 1-phenyl-lower alkoxycarbonyl, for example benzyloxycarbonyl, also an optionally substituted 1-polyphenyl-lower alkyl group, for example trityl, and furthermore the tetrahydropyranyl radical. Protecting groups located together at two adjacent hydroxy groups are for example: lower alkylidene, for example methylene or isopropylidene, or 1-phenyl-lower alkylidene, of which the phenyl moiety is optionally substituted by lower alkyl, such as by methyl or lower alkoxy, such as methoxy, particularly benzylidene, or cycloalkylidene, for example cyclopentylidene or cyclohexylidene, also the carbonyl group.

Groups of the stated types which can be split off by hydrolysis, for example acyl radicals of organic carboxylic acids, for example lower-alkanoyl radicals, also for example lower-alkoxycarbonyl or trityl radicals, also tetrahydropyranyl radicals, also lower-alkylidene, 1-phenyl-lower alkylidene or cycloalkylidene groups located together at two hydroxy groups, as well as optionally further protecting groups of this kind located at the nitrogen atom and/or at the oxygen atoms, can be split off, depending on the nature of such radicals, by treatment with water under acidic or basic conditions, for example in the presence of a mineral acid, such as hydrochloric acid or sulfuric acid, or of an hydroxide or carbonate of an alkali metal or alkaline-earth metal. A carbonyl group located at one of two adjacent hydroxy groups is advantageously split off by means of basic agents, for instance an alkali hydroxide, such as potassium hydroxide, or by means of an alkali metal alcoholate, such as sodium ethylate or potassium tert.-butylate, whilst for example tetrahydropyranyl radicals are split off by means of acid agents, for instance such as those mentioned. Radicals which can be split off by acidolysis are for example those mentioned above for $X_2$ and/or $X_4$, and are for example lower-alkoxycarbonyl or tert.-lower alkyl radicals. Radicals of this kind can be split off, for example as described above, by treatment with suitable strong organic carboxylic acids, such as by lower-alkanecarboxylic acids optionally substituted by halogen, especially fluorine, particularly by treatment with trifluoroacetic acid (if necessary in the presence of an activating agent, such as anisole), as well as with formic acid. These reactions are performed in a manner known per se.

A particularly suitable hydroxy protecting group that can be split off by hydrogenolysis is above all an α-aryllower alkyl group which can be split off by hydrogenolysis, such as an optionally substituted 1-polyphenyl-lower alkyl or 1-phenyl-lower alkyl group, wherein substituents, especially of the phenyl moiety, can be for example lower alkyl such as methyl, or lower alkoxy such as methoxy, and in particular benzyl. A group which is located at two adjacent hydroxyl groups together and which can be split off by hydrogenolysis is for example optionally substituted 1-phenyl-lower alkylidene, wherein substituents, especially of the phenyl moiety, can be for example lower alkyl such as methyl, or lower alkoxy such as methoxy, and particularly benzylidene. Groups of the stated type which can be split off by hydrogenolysis can be split off in the customary manner by treatment with catalytically activated hydrogen, for example with hydrogen in the presence of a nickel catalyst, such as Raney nickel, or of a suitable noble metal catalyst.

Protective groups which are located at one or two hydroxyl groups and which can be split off by means of reduction are for example those groups which are split off on being treated with a chemical reducing agent, for instance as described above, for example 2-halo-lower-alkoxycarbonyl or arylmethoxycarbonyl. Splitting off is effected for instance by the methods described above, for example by means of zinc, or of a chromium(II) salt, or by means of an organic carboxylic acid, such as formic acid.

Further protecting groups optionally present at the nitrogen atom and/or at the oxygen atoms correspond to the aforementioned groups that can be split off and replaced by hydrogen by the methods mentioned, whereby such groups can be split off in the course of the described process simulaneously with other groups or subsequently in a separate process step.

Starting materials of the formula IX wherein Ar₄ is substituted by a radical which can be converted into a hydroxy-lower alkyl group or polyhydroxy-lower alkyl group, such as a 1,2- or 2,3-dihydroxy-lower alkyl group, for example a 2,3-dihydroxypropyl group, can be obtained for example by a process wherein a compound which optionally carries protecting groups on the nitrogen atom and/or on the oxygen atoms and which corresponds to the formula IX in which Ar₄ is a group of the formula

or of the formula

wherein $R_9$ corresponds to a lower alkyl radical containing one carbon atom less, and $R_{10}$ to a lower alkyl radical containing two carbon atoms less, and $Z_3$ and $Z_4$, which can be identical or different, are each a reactive esterified hydroxy group, for example halogen, such as chlorine and particularly bromine, is reacted with a salt of a carboxylic acid, for example with an alkali metal salt, for instance the potassium salt, of a lower alkanecarboxylic acid, for example acetic acid, or of an aromatic carboxylic acid, such as benzoic acid, to give the corresponding compound of the formula IX containing one or two acyloxy groups in the lower alkyl group located at the radical Ar₄. Starting materials of the formula IX having a group IXa can be obtained by an addition reaction of for example hydrogen halide with an alkenyl radical bonded to the radical Ar, whereas starting materials having a group IXb are obtainable by an addition reaction of halogen, for example bromine, with an appropriate alkenyl radical.

Starting materials of the formula IX wherein Ar₄ is substituted for example by a group of the formula

in which $X°_{10}$ represents a radical which can be split off by hydrolysis, including alcoholysis or acidolysis, or by means of reduction, including hydrogenolysis, for example one of such radicals mentioned above, and $R_{10}$ has the meaning already defined, can be obtained by reacting for example a compound of the formula

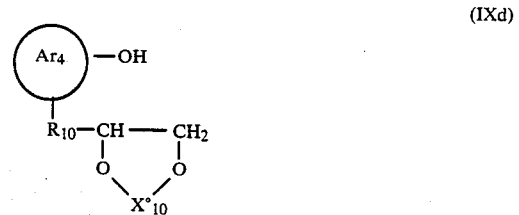

with epichlorohydrin, and reacting the resulting compound of the formula

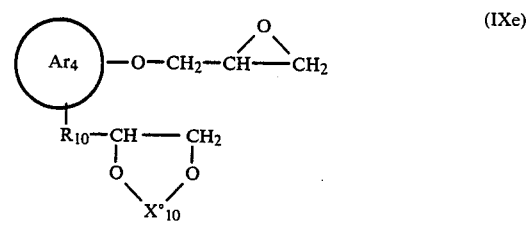

for example with a 5-(2-aminoethoxy)-salicylamide, which is optionally N-protected, such as N-benzylated, to obtain a compound of the formula IX wherein Ar₄ contains the group IXc.

These reactions are performed in the customary manner, optionally with cooling or heating, and in a suitable solvent.

When selecting one of the above suitable processes for the preparation of compounds of the formula I, care must be taken that substituents present, especially of the Ar radicals, are not converted or split off, should such conversions or splitting off be undesirable. Thus, especially functionally modified carboxyl groups, such as esterified or amidated carboxyl groups, and also cyano groups, as substituents of Ar radicals during solvolysis reactions, especially hydrolysis reactions, and also during reducing operations, may participate in the reaction and be converted. On the other hand, simultaneous conversion of substituents may be desirable; for example, unsaturated substituents, such as lower alkenyl, may be reduced, for example to lower alkyl, under the conditions of a reducing process used according to the invention.

Within the scope of the definition of the compounds of the formula I, compounds obtained in the usual manner according to the invention can be converted into other final products, for example by modifying introducing or splitting off suitable substituents in resulting compounds.

For instance, unsaturated substituents, for example lower alkenyl, in resulting compounds may be reduced, for example by treating with catalytically activated hydrogen.

Furthermore, in resulting compounds having halogen-substituted radicals of an aromatic nature, the halogen may be replaced by hydrogen, for example by treating with hydrogen in the presence of a customary hydrogenating catalyst, such as Raney nickel, or palladium on carbon.

Free carboxyl groups in the Ar radicals, may be esterified in the customary manner, for example by reacting with an appropriate alcohol, advantageously in the presence of an acid, such as a mineral acid, for example sulphuric acid or hydrochloric acid, or in the presence of a dehydrating agent, such as dicyclohexylcarbodiimide, or by reacting with a corresponding diazo compound, for example diazomethane. The esterification may also be carried out by reacting a salt, preferably an alkali metal salt of the acid, with a reactive esterified alcohol, for example an appropriate halide, such as chloride.

Free carboxyl groups may be amidated in the usual manner, for example by reaction with ammonia, or with a primary or secondary amine, advantageously in the presence of a dehydrating agent, such as dicyclohexyl carbodiimide or by converting the carboxyl group into a halocarbonyl group, for example a chlorocarbonyl group, and then reacting with ammonia or with a primary or secondary amine.

In compounds that contain an esterified carboxyl group, the latter may be converted into a free carboxyl group in the customary manner, for example by hydrolysis, preferably in the presence of strong bases, such as an alkali metal hydroxide, for example sodium or potassium hydroxide, or in the presence of strong acids, for example a strong mineral acid, such as a hydrohalic acid, for example hydrochloric acid, or sulphuric acid.

In compounds having an esterified carboxyl group as substituent, the latter may be converted into the corresponding carbamoyl group in the customary manner, for example by ammonolysis or aminolysis with ammonia or a primary or secondary amine.

Compounds having a carbamoyl group and preferably $R_1$ and $R_2$ radicals that do not represent hydrogen may be dehydrated to the corresponding cyano compounds in the customary manner, for example by the action of dehydrating agents, such as phosphorus pentoxide or phosphorus oxychloride, preferably at relatively high temperatures.

Compounds that contain a cyano substituent may be hydrolysed in the customary manner, for example in the presence of concentrated aqueous mineral acids, or alkali metal hydroxides, to the corresponding carbamoyl compounds, or directly to the carboxyl compounds.

Compounds having a cyano group as substituent may be alcoholysed to the corresponding compounds having esterified carboxyl groups in the customary manner, for example by the addition of alcohols in the presence of an anhydrous acid, such as hydrogen chloride, and by subsequent hydrolysis of the resulting imido ester.

As in the preparation processes, care must also be taken when carrying out the additional steps that undesirable side reactions that may result in the conversion of additional groupings, do not occur.

The above-described reactions may optionally be carried out at the same time or in succession, or in any sequence. If necessary, they are carried out in the presence of diluents, condensing agents and/or catalytically active agents, at reduced or elevated temperature, in a closed vessel under pressure and/or in an inert gas atmosphere.

Depending on the process conditions and starting substances, the new compounds are obtained in free form or in the form of their salts, also covered by the invention, wherein the new compounds or salts thereof may also be in the form of hemi-, mono-, sesqui- or polyhydrates. Acid addition salts of the new compounds may be converted into the free compounds in a manner known per se, for example by treating with basic agents, such as alkali metal hydroxides, carbonates or bicarbonates, or with ion-exchangers. On the other hand, resulting free bases with organic or inorganic acids, for example with the acids mentioned, may form acid addition salts, wherein the acids used for their preparation are especially those that are suitable for the formation of pharmaceutically acceptable salts.

These or different salts, especially acid addition salts of the new compounds, such as, for example, oxalates or perchlorates, may also be used for the purification of the resulting free bases, by converting the free bases into salts, separating them off and purifying them and liberating the bases from the free salts.

Depending on the choice of starting substances and working methods, the new compounds may be obtained as optical antipodes or racemates, or, provided they contain at least two asymmetric carbon atoms, as mixtures of racemates. The starting substances can also be used as specific optical antipodes.

Resulting mixtures of racemates may be separated into the two stereoisomeric (diastereoisomeric) racemates on the basis of physical-chemical differences in the diastereoisomers in known manner, for example by chromatography and/or fractional crystallisation.

Resulting racemates may be decomposed into the antipodes by methods known per se, for example by recrystallisation from an optically active solvent, by treating with suitable microorganisms, or by reacting with an optically active substance forming salts with the racemic compound, especially acids, and separating the salt mixture obtained in this manner, for example on the basic of different solubilities, into the diasteroisomeric salts, from which the free antipodes may be liberated by the action of suitable agents. Especially useful, optically active acids are, for example, the D- and L-forms of tartaric acid, di-O,O-(p-toluoyl)tartaric acid, malic acid, mandelic acid, camphorsulphonic acid, glutamic acid, aspartic acid or quinic acid. Advantageously, the more active of the two antipodes is isolated.

The invention relates also to those forms of the process according to which a compound that may be obtained as intermediate at any stage of the process is used as starting material, and the remaining process steps are carried out or the process is interrupted at any stage, or in which a starting substance is formed under the reaction conditions or in which a reactant is optionally present in the form of its salts.

Advantageously, the starting materials used for carrying out the reactions according to the invention are those which yield the groups of final substances mentioned initially, and especially those which lead to the specifically described or emphasized final substances.

The starting materials are known, or if they are new, can be prepared according to methods known per se, as described above, for example analogously to the Examples. The invention relates also to the new starting materials and to intermediates that may be obtained according to the process.

The new compounds may, for example, be used in the form of pharmaceutical preparations which contain a pharmacologically active amount of active substance, optionally together with pharmaceutically acceptable carriers that are suitable for enteral, for example oral, or parenteral, administration, and that may be organic or inorganic, solid or liquid. Thus, tablets or gelatin capsules are used which contain the active substance together with diluents, for example lactose, dextrose, sucrose, mannitol, sorbitol or cellulose and/or glycerin and/or lubricants, for example silica, talc, stearic acid or salts thereof, such as magnesium or calcium stearate, and/or polyethylene glycol. Tablets may likewise contain binders, for example magnesium aluminium silicate, starches, such as maize, corn, rice or arrow-root starches, gelatin, tragacanth, methylcellulose, sodium carboxymethylcellulose and/or polyvinylpyrrolidone, and, if desired, disintegrating agents, for example starches, agar, alginic acid, or a salt thereof, such as sodium alginate, and/or effervescing mixtures, or adsorption agents, colorants, flavouring substances and sweeteners. Furthermore, the new pharmacologically active compounds may be used in the form of parenterally administerable preparations or infusion solutions. Such solutions are preferably isotonic, aqueous solutions or suspensions, wherein these, for example in the case of lyophilised preparations that contain the active substance alone or together with a carrier, for example mannitol, can be prepared before use. The pharmaceutical preparations may be sterilised and/or contain auxiliaries, for example preservatives, stabilisers, wetting and/or emulsifying agents, solubilisers, salts for regulating the osmotic pressure and/or buffers. The present pharmaceutical preparations which, if desired, may contain other pharmacologically active substances, are prepared in a manner known per se, for example by means of conventional mixing, granulating, coating, dissolving, or lyophilising processes, and contain from approximately 0.1% to 100%, especially from approximately 1% to approximately 50%, and in the case of lyophilisates up to 100%, of the active substances.

The dosage may be dependent on various factors, such as the method of administration, species, age and individual condition. Thus, the doses to be administered orally to warm-blooded animals daily in one or more, preferably at most 4 individual doses, lie between 0.03 and 3 mg/kg for β-receptor blockers of the formula I, and, for warm-blooded animals of approximately 70 kg body weight, preferably between approximately 0.004 and approximately 0.08 g, and for β-receptor stimulators of the formula I, between 0.01 and 1 mg/kg and between approximately 0.002 and 0.04 g, respectively.

The following Examples serve to illustrate the invention; temperatures are given in degrees Centigrade.

EXAMPLE 1

21 g of crude 1[N-[2-(3-carbamoyl-4-hydroxyphenoxy)-1-methylethyl]benzylamino]-3-[4-(2-methoxyethoxy)phenoxy]propan-2-ol, dissolved in 170 ml of methanol, are hydrogenated with the addition of 2 g of Pd/C-catalyst (5%) under normal conditions until hydrogen absorption ceases. By filtration and concentration of the solution by evaporation, an oil is obtained which crystallises when triturated with toluene. After recrystallisation of the crystalline residue from ethyl acetate, the resulting 1-[2-(3-carbamoyl-4-hydroxphenoxy)-1-methylethylamino]-3-[4-(2-methoxyethoxy)phenoxy]-propan-2-ol melts at 117°–125°, (mixture of the diastereoisomers).

The starting material is prepared as follows:

(1a) In accordance with the method described by Irvine et al., Synthesis 1972, 568, using an excess of acetone, 2,5-dihydroxybenzamide is converted into 2,3-dihydro-2,2-dimethyl-6-hydroxy-4H-1,3-benzoxazin-4-one having a melting point of 215°–216°.

(1b) 70 g of 2,3-dihydro-2,2-dimethyl-6-hydroxy-4H-1,3-benzoxazin-4-one are refluxed for 30 hours, whilst stirring, in 400 ml of acetonitrile with 100 g of potassium carbonate and 32 ml of chloroacetone. After the addition of a further 3.2 ml of chloroacetone, the reaction mixture is heated for a further 15 to 20 hours. The still warm reaction mixture is filtered, the residue thoroughly washed with acetone and the combined filtrate is concentrated by evaporation. The crystalline residue is recrystallised from toluene and yields 2,3-dihydro-2,2-dimethyl-6-(2-oxopropoxy)-4H-1,3-benzoxazin-4-one having a melting point of 125°–126°.

(1c) 74 g of crude 2,3-dihydro-2,2-dimethyl-6-(2-oxopropoxy)-4H-1,3-benzoxazin-4-one obtained according to Example (1b) are heated in a mixture of 150 ml of dioxan and 450 ml of 2N hydrochloric acid for 45 minutes on a water bath. The solvent is evaporated off and the crystalline residue triturated with water and then suction-filtered. By recrystallisation from isopropanol, 5-(2-oxopropoxy)salicylamide having a melting point of 152°–154° is obtained.

(1d) 55 g of benzylamine and 1.25 g of concentrated sulphuric acid are added to a solution of 104.5 g of 5-(2-oxopropoxy)salicylamide in 100 ml of methanol and hydrogenated in the presence of 3.0 g of Pt/C-catalyst at room temperature and atmospheric pressure until 1 equivalent of hydrogen has been absorbed. The catalyst is filtered off, approximately 10 g of powdered calcium carbonate are stirred into the solution and the solution is filtered again and concentrated by evaporation. The oil remaining crystallises from isopropanol. Repeated recrystallisation from isopropanol yields 5-[2-(benzylamino)propoxy]-salicylamide having a melting point of 102°–104°.

(1e) A solution of 10.2 g of 1-(2,3-epoxypropoxy)-4-(2-methoxyethoxy)benzene and 11.0 g of 5-[2-(benzylamino)propoxy]salicylamide in 200 ml of isopropanol is refluxed for 24 hours. By concentration of the solution by evaporation, crude 1-[N-[2-(3-carbamoyl-4-hydroxyphenoxy)-1-methylethyl]benzylamino]-3-[4-(2-methoxyethoxy)phenoxy]propan-2-ol is obtained as an oil which is used in its crude state for debenzylation.

EXAMPLE 2

6.1 g of crude 1-[N-[2-(4-carbamoyl-3-hydroxyphenoxy)-1-methylethyl]benzylamino]-3-[4-(2-methoxyethoxy)phenoxy]propan-2-ol are hydrogenated and worked up analogously to Example 1. After recrystallisation from isopropanol, 1-[2-(4-carbamoyl-3-hydroxyphenoxy)-1-methylethylamino]-3-[4-(2-methoxyethoxy)phenoxy]propan-2-ol is obtained as a diastereoisomeric mixture having a melting point of 120°–121°.

The starting material is prepared as follows:

(2a) Analogously to Example (1a), from 2,4-dihydroxybenzamide there is obtained 2,3-dihydro-2,2-dimethyl-7-hydroxy-4H-1,3-benzoxazin-4-one having a melting point of 249°–251°.

(2b) Analogously to Example (1b), from 168 g of 2,3-dihydro-2,2-dimethyl-7-hydroxy-4H-1,3-benzoxazin-4-one, 305 g of potassium carbonate and 88 ml of chloroacetone in 1.2 liters of acetonitrile, there is obtained by boiling for 28 hours and subsequent working up, 2,3-dihydro-2,2-dimethyl-7-(2-oxopropoxy)-4H-1,3-benzoxazin-4-one having a melting point of 160°–162° (from isopropanol).

(2c) 75 g of crude 2,3-dihydro-2,2-dimethyl-7-(2-oxopropoxy)-4H-1,3-benzoxazin-4-one and 32 g of benzylamine, dissolved in 1000 ml of methanol, are hydrogenated under normal conditions with the addition of 0.75 g of concentrated sulphuric acid and 1.6 g of Pt/C-catalyst (5%) until hydrogen absorption ceases. After filtering off the catalyst and evaporating off the solvent, the oily residue is divided between 300 ml of ethyl acetate and 500 ml of 2N hydrochloric acid. Crude 2,3-dihydro-2,2-dimethyl-7-[(2-benzylamino)propoxy]-4H-1,3-benzoxazin-4-one is isolated as an oil from the aqueous phase by rendering alkaline with concentrated ammonia (whilst cooling with ice) and extracting with ethyl acetate, and this oil can be put to further use in its crude state.

(2d) A mixture of 100 g of crude 2,3-dihydro-2,2-dimethyl-7-[(2-benzylamino)propoxy]-4H-1,3-benzoxazin-4-one, 100 ml of isopropanol and 100 ml of isopropylamine is refluxed for 1 hour and then concentrated by evaporation. The oil remaining crystallises when triturated with ether. The crystals are suction-filtered and washed with a little isopropanol. In this manner, 4-[2-benzylamino)propoxy]salicylamide having the melting point of 121°–123° is obtained.

(2e) Analogously to Example (1e), using 4-[2-(benzylamino)propoxy]salicylamide instead of the 5-derivative, 1-[N-[2-(4-carbamoyl-3-hydroxyphenoxy)-1-methylethyl]benzylamino]-3-[4-(2-methoxyethoxy)phenoxy]propan-2-ol is obtained as an oil which is used in its crude state for debenzylation.

EXAMPLE 3

Analogously to Example 2, by debenzylation of 22 g of crude 1-[N-[2-(3-carbamoyl-4-hydroxyphenoxy)ethyl]benzylamino]-3-[2-[N-(2-hydroxyethyl)carbamoylmethoxy]phenoxy]propan-2-ol there is obtained 1-[2-(3-carbamoyl-4-hydroxyphenoxy)ethylamino]-3-[2-[N-(2-hydroxyethyl)carbamoylmethoxy]phenoxy]propan-2-ol having a melting point of 157°–159°. A hydrochloride is formed having a melting point of 126°–127° (from isopropanol/water 1:1).

The starting material is obtained in the following manner:

(3a) A mixture of 48.2 g of 2,3-dihydro-2,2-dimethyl-6-hydroxy-4H-1,3-benzoxazin-4-one, 70 g of potassium carbonate and 250 ml of 1,2-dibromoethane is refluxed for 4 hours whilst stirring. The semi-liquid reaction mixture is extracted 3 to 4 times whilst hot with 1 liter of methanol each time; the combined methanol extracts are concentrated by evaporation and the residue is recrystallised from methanol. 6-(2-Bromoethoxy)-2,3-dihydro-2,2-dimethyl-4H-1,3-benzoxazin-4-one having a melting point of 190°–195° is obtained.

(3b) A mixture of 60 g of 6-(2-bromoethoxy)-2,3-dihydro-2,2-dimethyl-4H-1,3-benzoxazin-4-one and 110 ml of benzylamine is stirred for 30 minutes in a bath at 80°. The reaction mixture is then brought to pH 3–4 with concentrated hydrochloric acid, whilst cooling with ice, and left to crystallise. After 2–4 hours, the crystals are suction-filtered, washed with 50 ml of water and 50 ml of ethyl acetate and dried. The resulting 5-[(2-benzylamino)ethoxy]salicylamide hydrochloride melts at 214°–216°. The base liberated therefrom melts at 107°–108° (from ethyl acetate/ether).

(3c) 12 g of [2-(2,3-epoxypropoxy)phenoxy]-N-(2-hydroxyethyl)acetamide and 11.5 g of 5-[(2-benzylamino)ethoxy]salicylamide are refluxed in 70 ml of isopropanol for 18–24 hours. The oily residue of evaporation is used for debenzylation in its crude state.

EXAMPLE 4

21 g of crude 1-[N-[2-(3-carbamoyl-4-hydroxyphenoxy)ethyl]benzylamino]-3-[4-(2-methoxyethoxy)phenoxy]propan-2-ol are hydrogenated analogously to Example 1. After hydrogen absorption has ceased, the product is dissolved in hot methanol and the catalyst is filtered off. By concentration of the methanolic solution by evaporation, 1-[2-(3-carbamoyl-4-hydroxyphenoxy)ethylamino]-3-[4-(2-methoxyethoxy)phenoxy]propan-2-ol is obtained as crystals having a melting point of 157°–158°. A neutral fumarate is formed having a melting point of 150°–151° (from methanol/acetone).

The starting material may be prepared as follows:

(4a) A solution of 9 g of 1-(2,3-epoxypropoxy)-4-(2-methoxyethoxy)benzene and 8.6 g of 5-[(2-benzylamino)ethoxy]salicylamide in 60 ml of isopropanol is refluxed for 24 hours. The crude product obtained by concentration by evaporation is divided between 50 ml of 2N hydrochloric acid and 100 ml of ether. The aqueous phase is separated off, and rendered alkaline with concentrated ammonia solution whilst cooling with ice. By extraction with approximately 300 ml of ethyl acetate, drying (MgSO4), and concentration by evaporation, the crude 1-[N-[2-(3-carbamoyl-4-hydroxyphenoxy)ethyl]benzylamino]-3-[4-(2-methoxyethoxy)phenoxy]propan-2-ol is isolated as an oil and used without further purification for debenzylation.

EXAMPLE 5

The following are prepared in a manner analogous to Examples 4 and (4a):

1-[2-(3-carbamoyl-4-hydroxyphenoxy)ethylamino]-3-phenoxypropan-2-ol, melting point 154°–156°, (from methanol, 1-[2-(3-carbamoyl-4-hydroxyphenoxy)ethylamino]-3-[4-[2-(methoxycarbonylamino)ethoxy]phenoxy]propan-2-ol, melting point 150°–151°, (from methanol), 1-(4-acetamidophenoxy)-3-[2-(3-carbamoyl-4-hydroxyphenoxy)ethylamino]propan-2-ol, melting point 185° (from methanol), 1-[2-(3-carbamoyl-4-hydroxyphenoxy)ethylamino]-3-(2-methylphenoxy)propan-2-ol, melting point 129°–130°, (from isopropanol), 1-[2-(3-carbamoyl-4-hydroxyphenoxy)ethylamino]-3-(3-methylphenoxy)propan-2-ol, melting point 154°–155° (from methanol), 1-[2-(3-carbamoyl-4-hydroxyphenoxy)-5-ethylamino]-3-(2-methylindol-4-yloxy)propan-2-ol, melting point 180°–194° (from ethyl acetate), 5-[3-[2-(3-carbamoyl-4-hydroxyphenoxy)ethylamino]-2-hydroxypropoxy]-1,2,3,4-tetrahydro-2,3-cis-naphthalenediol as diastereoisomeric mixture, melting point 108°–118° (from methanol), 4-[2-hydroxy-3-[(3-carbamoyl-4-hydroxyphenoxy)ethylamino]propoxy]phenylacetamide, melting point 149°-151° (from methanol); a different crystal modification has a melting point of 181°-182° (from dimethylformamide/water), 4-[2-hydroxy-3-[(3-carbamoyl-4-hydroxyphenoxy)ethylamino]propoxy]phenoxyacetamide melting point 168°-170° (from DMF/water), N-[4-[2-hydroxy-3-[(3-carbamoyl-4-hydroxyphenoxy)ethylamino]propoxy]phenyl]-N',N'-dimethyl urea, melting point 140°-142° (with decomposition) (from methanol), 1-(4-butyroylamino-2-acetylphenoxy)-3-[2-(3-carbamoyl-4-hydroxyphenoxy)ethylamino]propan-2-ol, 1-[2-(3-carbamoyl-4-hydroxyphenoxy)ethylamino]-3-(2-methoxyphenoxy)propan-2-ol, melting point 125°-126°, (from methanol), 1-[2-(3-carbamoyl-4-hydroxyphenoxy)ethylamino]-3-(2,3-dimethylphenoxy)propan-2-ol, melting point 129°-131° (from methanol), 1-[2-(3-carbamoyl-4-hydroxyphenoxy)ethylamino]-3-[2-(2-methoxyethoxy)phenoxy]propan-2-ol, melting point of the hydrochloride 157°-160° (from methanol-acetone), 1-[2-(3-carbamoyl-4-hydroxyphenoxy)ethylamino]-3-[3-(2-methoxyethoxy)phenoxy]propan-2-ol, 1-[2-(3-carbamoyl-4-hydroxyphenoxy)ethylamino]-3-[2-(pyrrol-1-yl)phenoxy]propan-2-ol, melting point 138°-140° (sinters at temperatures of 135° and above), 1-(2-carbamoylphenoxy)-3-[2-(3-carbamoyl-4-hydroxyphenoxy)ethylamino]propan-2-ol, melting point of hydrochloride 149°-152° (from methanol), 1-[2-(3-carbamoyl-4-hydroxyphenoxy)ethylamino]-3-(3-trifluoromethylphenoxy)propan-2-ol, melting point 195°-196° (from methanol), 1-(2-acetylphenoxy)-3-[2-(3-carbamoyl-4-hydroxyphenoxy)ethylamino]propan-2-ol, melting point 122°-124° (from isopropanol), 1-[4-[2-(acetamido)ethoxy]phenoxy]-3-[2-(3-carbamoyl-4-hydroxyphenoxy)ethylamino]propan-2-ol as a hydrochloride, melting point 191°-192° (from methanol), 1-[2-(3-carbamoyl-4-hydroxyphenoxy)ethylamino]-3-(3-methylpyridin-2-yloxy)propan-2-ol, melting point 147°-148° (from methanol, 1-[2-(3-carbamoyl-4-hydroxyphenoxy)ethylamino]-3-(3-methyl-4-methylsulphonylphenoxy)propan-2-ol, melting point 128°-131° (from acetonitrile), 1-[2-(3-carbamoyl-4-hydroxyphenoxy)ethylamino]-3-(1-naphthyloxy)propan-2-ol, melting point 131°-134° (from isopropanol).

EXAMPLE 6

Analogously to Examples 2 and (2e), from 10.5 g of 4-[(2-benzylamino)propoxy]salicylamide and 8.5 g of 3,4-dihydro-5-(2,3-epoxypropoxy)-2-(1H)-quinolinone and by debenzylating the reaction product, there is obtained 5-[3-[2-(4-carbamoyl-3-hydroxyphenoxy)-1-methylethylamino]-2-hydroxypropoxy]-3,4-dihydro-2-(1H)-quinolinone as a diastereoisomeric mixture which forms a hydrochloride having a melting point of 239°-245° (from methanol).

EXAMPLE 7

A solution of 16 g of crude 1-[N-[3-(3-carbamoyl-4-hydroxyphenyl)propyl]benzylamino]-3-[4-(2-methoxyethoxy)phenoxy]propan-2-ol is hydrogenated analogously to Example 1. The hydrogenating solution is neutralised with a solution of hydrochloric acid gas in methanol, concentrated by evaporation and crystallised from acetone. In this manner 1-[3-(3-carbamoyl-4-hydroxyphenyl)propylamino]-3-[4-(2-methoxyethoxy)phenoxy]propan-2-ol is obtained as a hydrochloride having a melting point of 194°-200°.

The starting material may be prepared as follows:

(7a) 3-(4-hydroxyphenyl)propionic acid is converted into the mixed anhydride and then, with benzylamine, into the 3-(4-hydroxyphenyl)propionic acid N-benzylamide (m.p. 115°-116°).

(7b) Flask-synthesis ($CO_2$, 180°, 4 hours, 55 bar) with the sodium salt of the compound prepared according to (7a) yields 3-(3-carboxy-4-hydroxyphenyl)propionic acid N-benzylamide having a melting point of 180°-181°.

(7c) Esterification with methanol/sulphuric acid while refluxing for 48 hours yields 3-(3-methoxycarbonyl-4-hydroxyphenyl)propionic acid N-benzylamide having a melting point of 139°-140° (from ethyl acetate).

(7d) Reacting with benzyl bromide/potassium carbonate in acetone (refluxing for 15 hours) yields 3-(4-benzyloxy-3-methoxycarbonylphenyl)propionic acid N-benzylamide as a yellowish oil.

(7e) Selective reduction of the amide group with diborane in tetrahydrofuran (for 48 hours, 20°-25°) with gentle catalytic debenzylation of the product (Pd/C-catalyst 5%, 15°-20° in methanol) yield N-[3-(4-hydroxy-3-methoxycarbonylphenyl)propyl]benzylamine having a melting point of 75°-77° (from isopropanol).

(7f) 200 ml of concentrated ammonia are added to a solution of 27 g of N-[2-(4-hydroxy-3-methoxycarbonylphenyl)propyl]benzylamine in 100 ml of dioxan and the solution is left to stand for 3-4 days at 20°-30°. The reaction mixture is concentrated by evaporation, divided between water and ethyl acetate and the organic phase is separated. Usual working up yields crude N-[3-(3-carbamoyl-4-hydroxyphenyl)propyl]benzylamine as an oil which is processed further without further purification.

(7g) A solution of 6.7 g of 1-(2,3-epoxypropoxy)-4-(2-methoxyethoxy)benzene and 8.5 g of N-[3-(3-carbamoyl-4-hydroxyphenyl)propyl]benzylamine in 70 ml of isopropanol is refluxed for 18 hours and then concentrated by evaporation. The resulting crude 1-[N-[3-(3-carbamoyl-4-hydroxyphenyl)propyl]benzylamino]-3-[4-(2-methoxyethoxy)phenoxy]propan-2-ol is used in its crude state for debenzylation.

EXAMPLE 8

A solution of 5 g of crude 1-[N-[2-(3-carbamoyl-4-hydroxyphenoxy)-1-methylethyl]benzylamino]-3-(4-benzyloxyphenoxy)propan-2-ol (with diastereoisomer pair A present in greater amount) in 50 ml of methanol is hydrogenated under normal conditions in the presence of 0.5 g of Pd/C-catalyst (5%) until 2 equivalents of hydrogen have been absorbed, whereupon the hydrogenation ceases. The reaction mixture is filtered, 0.52 g of fumaric acid is dissolved in the filtrate and the solution is concentrated to approximately 10 ml. After standing for a relatively long period of time, crystals of the neutral fumarate of 1-[2-(3-carbamoyl-4-hydroxyphenoxy)-1-methylethylamino]-3-(4-hydroxyphenoxy)propan-2-ol form, having a melting point of 195°-198° (pure enantiomer pair A).

In an analogous manner, by debenzylation of the enantiomer pair B present in greater amount the fumarate of the pure enantiomer pair B having a melting point of 181°–185° can be prepared.

The starting materials can be prepared as follows:

(8a) A solution of 49.8 g of 2,3-dihydro-2,2-dimethyl-6-(2-oxopropoxy)-4H-1,3-benzoxazin-4-one and 21.4 g of benzylamine in 700 ml of methanol is hydrogenated with the addition of 0.5 g of concentrated sulphuric acid and 3 g of Pt/C-catalyst (5%) until the equivalent amount of hydrogen has been asborbed. Working up analogously to Example (1d) yields 6-(2-benzylaminopropoxy)-2,3-dihydro-2,2-dimethyl-4H-1,3-benzoxazin-4-one having a melting point of 127°–129° (from isopropanol).

(8b) A solution of 15.4 g of benzyl [4-(2,3-epoxypropoxy)phenyl]ether and 17.0 g of 6-(2-benzylaminopropoxy)-2,3-dihydro-2,2-dimethyl-4H-1,3-benzoxazin-4-one in 100 ml of isopropanol is refluxed for 24 hours, filtered and concentrated by evaporation. Trituration of the residue with approximately 200 ml of ether results in crystallisation of 1-[N-[2-(2,3-dihydro-2,2-dimethyl-4-oxo-4H-1,3-benzoxazin-6-yloxy)-1-methylethyl]benzylamino]-3-(4-benzyloxyphenoxy)-propan-2-ol having a melting point of 149°–160° (in which the enantiomer pair A is present in greater amount).

By concentrating the ether solution by evaporation and recrystallising from a little isopropanol, after standing for several days crystals having a melting point of 59°–62° (rest up to 140°) are obtained. The mother liquor which no longer crystallises is separated off. It contains the enantiomer pair B in greater amount.

(8c) 5.2 g of the crystals having a melting point of 149°–160° mentioned under (8b) are refluxed in a mixture of 20 ml of isopropylamine and 40 ml of isopropanol for 1 hour and then concentrated by evaporation. The resulting crude 1-[N-[2-(3-carbamoyl-4-hydroxyphenoxy)-1-methylethyl]-benzylamino]-3-(4-benzyloxyphenoxy)propan-2-ol (5 g) obtained as an oil contains the enantiomer pair A in greater amount and is used without further purification for debenzylation.

The procedure with the oil from Example (8b) containing the enantiomer pair B in greater amount is analogous.

EXAMPLE 9

80 ml of isopropylamine are added to a solution of 18.0 g of crude 1-[2-(2,3-dihydro-2,2-dimethyl-4-oxo-4H-1,3-benzoxazin-6-yloxy)-1-methylethylamino]-3-(4-methylcarbamoylphenoxy)propan-2-ol in 300 ml of methanol and the solution is refluxed for 1 hour. The reaction mixture is concentrated by evaporation and the oil remaining is crystallised from 80 ml of isopropanol. 1-[2-(3-Carbamoyl-4-hydroxyphenoxy)-1-methylethylamino]-3-(4-methylcarbamoylphenoxy)propan-2-ol having a melting point of 172°–175° (diastereoisomeric mixture) is obtained.

The starting materials can be obtained as follows:

(9a) A solution of 13.6 g of 6-(2-benzylaminopropoxy)-2,3-dihydro-2,2-dimethyl-4H-1,3-benzoxazin-4-one and 10.4 g of 4-(2,3-epoxypropoxy)-N-methylbenzamide in 80 ml of isopropanol is refluxed for 30 hours. The residue remaining after the solvent has been evaporated off is divided between ether and 2N hydrochloric acid. The acidic, aqueous phase is separated off, and, whilst cooling with ice, rendered alkaline with approximately 10% aqueous ammonia solution and extracted with ethyl acetate. By separating off, drying (MgSO$_4$) and concentrating the ethyl acetate extract by evaporation, the crude 1-[N-[2-(2,3-dihydro-2,2-dimethyl-4-oxo-4H-1,3-benzoxazin-6-yloxy)-1-methylethyl]benzylamino]-3-(4-methylcarbamoylphenoxy)propan-2-ol is obtained as an oil which may be used without further purification for catalytic debenzylation.

(9b) The product obtained according to (9a) is dissolved in 300 ml of methanol and, with the addition of 2.8 g of Pd/C-catalyst (5%) and a further addition of 1.4 g of catalyst, is hydrogenated until hydrogen absorption ceases. The methanolic solution of 1-[2-(2,3-dihydro-2,2-dimethyl-4-oxo-4H-1,3-benzoxazin-6-yloxy)-1-methylethylamino]-3-(4-methylcarbamoylphenoxy)propan-2-ol obtained after the catalyst has been filtered off is further processed directly.

EXAMPLE 10

Exactly in accordance with the method described in Example 9, using 4-(2,3-epoxypropoxy)-(2-methoxyethyl)benzene, 1-[2-(3-carbamoyl-4-hydroxyphenoxy)-1-methylethylamino]-3-[4-(2-methoxyethyl)phenoxy]propan-2-ol is obtained as a diastereoisomeric mixture having a melting point of 139°–142° (from ethyl acetate).

EXAMPLE 11

A mixture of 9.0 g of 6-(2-bromoethoxy)-2,3-dihydro-2,2-dimethyl-4H-1,3-benzoxazin-4-one and 14.5 g of 1-(2-allyloxyphenoxy)-3-aminopropan-2-ol is stirred for 1 hour in a bath at 110°–120°. The melt is then extracted by boiling with 100 ml of isopropanol, the solution is filtered and concentrated by evaporation. The residue is divided between 400 ml of ethyl acetate and 50 ml of 2N potassium bicarbonate solution. By concentration by evaporation and fractional crystallisation, 1-(2-allyloxyphenoxy)-3-[2-(3-carbamoyl-4-hydroxyphenoxy)ethylamino]propan-2-ol having a melting point of 147°–148° (from isopropanol) is obtained from the ethyl acetate solution. The neutral fumarate of the compound melts at 136°–137° (from methanol).

EXAMPLE 12

A mixture of 11.2 g of 1-(2-allyloxyphenoxy)-3-aminopropan-2-ol and 10.5 g of 5-(2-oxopropoxy)-salicylamide is boiled using a water separator in 200 ml of toluene with the addition of a few drops of acetic acid. After the splitting off of water has ceased (after about 2–3 hours), the solution is concentrated by evaporation, the dark red residue is dissolved in 300 ml of ethanol and a total of 5.7 g of sodium borohydride is added in portions whilst stirring. The temperature increases during this operation to 36°. The reaction mixture is stirred for a further 2 hours at 20°–30°, and left to stand overnight. Whilst cooling with ice, it is then brought to pH 3–4 with approximately 6N hydrochloric acid, filtered and concentrated by evaporation. The residue is divided between 100 ml of water and 100 ml of ethyl acetate, the aqueous phase is separated off, rendered alkaline with concentrated ammonia and extracted with 200 ml of ethyl acetate. Working up of the organic phase yields crude oily 1-(2-allyloxyphenoxy)-3-[2-(3-carbamoyl-4-hydroxyphenoxy)-1-methylethylamino]propan-2-ol as an enantiomer mixture. By slow crystallisation from isopropanol the two pure enantiomer pairs having melting points of 123°–125° and 98°–102° respectively are obtained.

EXAMPLE 13

A mixture of 6.5 g of 5-(2-bromoethoxy)salicylamide and 8.9 g of 1-(2-allyloxyphenoxy)-3-aminopropan-2-ol is melted in an oil bath at 100° and stirred for 1 hour using a magnetic stirrer. The working up is carried out analogously to Example 11 and yields 1-(2-allyloxyphenoxy)-3-[2-(3-carbamoyl-4-hydroxyphenoxy)ethylamino]propan-2-ol having a melting point of 147°–148° (from isopropanol).

The salicylamide compound used as starting material may be obtained as follows:

(13a) 30.0 g of 6-(2-bromoethoxy)-2,3-dihydro-2,2-dimethyl-4H-1,3-benzoxazin-4-one are refluxed in a mixture of 100 ml of dioxan and 100 ml of 6N hydrochloric acid, whilst stirring, for 1.5 hours. The crystals obtained after concentrating the reaction mixture by evaporation are washed with 50 ml of water and dried in vacuo. The resulting 5-(2-bromoethoxy)salicylamide melts at 141°–143°.

EXAMPLE 14

By using the corresponding 1-aryloxy-3-aminopropan-2-ols the following compounds are obtained in a manner analogous to Example 13:

1-[2-(3-carbamoyl-4-hydroxyphenoxy)ethylamino]-3-(2-cyanophenoxy)propan-2-ol, melting point 121°–124° (from ethanol), 1-[2-(3-carbamoyl-4-hydroxyphenoxy)ethylamino]-3-[4-(2-methoxyethoxy)phenoxy]propan-2-ol, melting point 157°–158° (from isopropanol), 1-[2-(3-carbamoyl-4-hydroxyphenoxy)ethylamino]-3-[2-(prop-2-ynyloxy)phenoxy]propan-2-ol, melting point 140°–141° (from ethanol), 1-[2-(3-carbamoyl-4-hydroxyphenoxy)ethylamino]-3-[4-(2-methylthioethoxy)phenoxy]propan-2-ol, which forms a hydrochloride having a melting point of 202°–204° (from methanol), 1-[2-(3-carbamoyl-4-hydroxyphenoxy)ethylamino]-3-[2-allylphenoxy]propan-2-ol, which forms a neutral fumarate having a melting point of 165°–166° (from ethanol).

EXAMPLE 15

Analogously to Example 1, by debenzylation of 16 g of crude 1-[N-[2-(3-carbamoyl-4-hydroxyphenoxy)-1-methylethyl]benzylamino]-3-[4-(carbamoylmethoxy)-phenoxy]-propan-2-ol, after crystallisation from dioxan the pure 1-[2-(3-carbamoyl-4-hydroxyphenoxy)-1-methylethylamino]-3-[4-(carbamoylmethoxy)phenoxy]-propan-2-ol having a melting point of 145°–149° is obtained (sinters at a temperature of 140°) (mixture of the diastereoisomers).

EXAMPLE 16

Analogously to Example 3, by debenzylation of 18 g of crude 1-[N-[2-(3-carbamoyl-4-hydroxyphenoxy)ethylbenzylamino]-3-[2-[N'-(2-hydroxyethyl)ureidomethyl]phenoxy]-propan-2-ol, after crystallisation from dimethylformamide/ether 1-[2-(3-carbamoyl-4-hydroxyphenoxy)ethylamino]-3-[2-[N'-(2-hydroxyethyl)ureidomethyl]phenoxy]propan-2-ol is obtained having a melting point of 164°–166°.

The starting material can be prepared as follows:

2-benzyloxybenzylamine:

In a Soxhlet apparatus 18.4 g of lithium aluminium hydride in 1800 ml of dry ether are boiled under a nitrogen atmosphere at a bath temperature of 70°, 5.3 g of 2-benzyloxybenzamide being introduced into the Soxhlet thimble. After 21 hours the reaction mixture is immersed in an ice bath, and 18.4 ml of water, 18.4 ml of 15% sodium hydroxide solution and 55 ml of water are added dropwise in succession, whilst stirring. The temperature may be allowed to rise to a maximum of +10°. Stirring of the mixture is then continued at 20° and the resulting precipitate is suction-filtered and washed with ether. The filtrate is concentrated by evaporation in vacuo and the oil remaining is stirred with 500 ml of 10% hydrochloric acid and 400 ml of ether for 2 hours, whilst cooling with ice. The precipitated 2-benzyloxybenzylamine hydrochloride is suction-filtered, washed with water and ether and dried in vacuo. Melting point 190°–191°.

2-benzyloxybenzyl isocyanate:

38.5 g of 2-benzyloxybenzylamine hydrochloride are suspended in 400 ml of distilled toluene and heated at a bath temperature of 140°. Whilst stirring, phosgene is introduced and after about 50 minutes the solution becomes clear. After a further 10 minutes, the addition of phosgene is interrupted and boiling is continued for a further hour. The solution is then left to cool a little and the toluene is distilled off in vacuo. A sample of the oil remaining was distilled in a bulb tube: Boiling point, bath temperature 120°/0.06 torr.

N-(2-hydroxyethyl)-N'-(2-benzyloxybenzyl)urea:

A solution of 73.6 g of crude 2-benzyloxybenzyl isocyanate in 120 ml of methylene chloride is added dropwise in the course of 50 minutes in a solution of 36.8 ml of ethanolamine in 370 ml of methylene chloride. The reaction is slightly exothermic. After 2 hours the reaction solution is washed three times with 200 ml of water each time and dried using sodium sulphate. Methylene chloride is distilled off and the residue is recrystallised from isopropanol. The resulting product melts at 92°–94°.

N-(2-hydroxyethyl)-N'-(2-hydroxybenzyl)urea:

59.6 g of N-(2-hydroxyethyl)-N'-(2-benzyloxybenzyl)urea are dissolved in 600 ml of methanol and hydrogenated in the presence of 6 g of Pd/C-catalyst (5%). After 2 hours the hydrogenation ceases. The catalyst is suction-filtered, and the filtrate concentrated by evaporation in vacuo. The residue is recrystallised from 350 ml of ethyl acetate; the pure product melts at 100°–101°.

N-[2-(2,3-epoxypropoxy)benzyl]-N'-(2-hydroxyethyl)urea:

A mixture of 29.2 g of N-(2-hydroxyethyl)-N'-(2-hydroxybenzyl)urea, 440 ml of epichlorohydrin and 38.9 g of potassium carbonate is stirred for 6 hours at 90°. The solids are then suction-filtered whilst hot, washed with acetonitrile and the filtrate is concentrated by evaporation in vacuo. The oil remaining crystallises when left to stand and is recrystallised from 320 ml of ethyl acetate, with carbon treatment. The resulting epoxide melts at 96°–99°.

1-[N-[2-(3-carbamoyl-4-hydroxyphenoxy)ethyl]benzylamino]-3-[2-[N'-(2-hydroxyethyl)ureidomethyl]-phenoxy]propan-2-ol:

A solution of 9.75 g of the above epoxide and 9.4 g of N-[(3-carbamoyl-4-hydroxyphenoxy)ethyl]benzylamine in 100 ml of isopropanol is stirred for 7 hours at a bath temperature of 95°. The solution is concentrated by evaporation in vacuo. The resulting crude product can be subjected directly to hydrogenolysis.

EXAMPLE 17

A mixture of 10.2 g of [2-(2,3-epoxypropoxy)phenyl]-prop-2-ynyl ether, 7.8 g of 5-(2-aminoethoxy)salicylamide and 25 ml of isopropanol is refluxed for 1 hour whilst stirring. The residue remaining after concentrating the reaction mixture by evaporation is dissolved in 30 ml of ethyl acetate. The 1-[2-(3-carbamoyl-4-hydroxyphenoxy)ethylamino]-3-[2-(prop-2-ynyloxy)phenoxy]-propan-2-ol crystallising out melts after recrystallisation from ethanol at 140°–141°.

(17a) The 5-(2-aminoethoxy)salicylamide required as starting material can be prepared by debenzylation, using hydrogen in the presence of a Pd/C-catalyst (5%), of the corresponding N-benzyl compound (analogously to Example (3b) in methanol; it melts at 140°.

EXAMPLE 18

Analogously to Example 17, by using the correspondingly substituted epoxides, the following compounds are obtained:
1-[2-(3-carbamoyl-4-hydroxyphenoxy)ethylamino]-3-(2-cyanophenoxy)propan-2-ol, melting point 121°–124° (from ethanol),
1-[2-(3-carbamoyl-4-hydroxyphenoxy)ethylamino]-3-(2-chlorophenoxy)propan-2-ol, melting point 140°–141° (from ethanol),
1-[2-(3-carbamoyl-4-hydroxyphenoxy)ethylamino]-3-[4-(2-methylthioethoxy)phenoxy]propan-2-ol, which forms a hydrochloride, melting point 202°–204°, (from methanol),
1-(2-allylphenoxy)-3-[2-(3-carbamoyl-4-hydroxyphenoxy)ethylamino]propan-2-ol, the neutral fumarate of which melts at 165°–166° (from ethanol),
1-[2-(3-carbamoyl-4-hydroxyphenoxy)ethylamino]-3-[4-(2-methoxyethoxy)phenoxy]propan-2-ol, melting point 157°–158° (from methanol),
1-(2-allyloxyphenoxy)-3-[2-(3-carbamoyl-4-hydroxyphenoxy)ethylamino]propan-2-ol, melting point 147°–148° (from methanol),
1-[2-(3-carbamoyl-4-hydroxyphenoxy)ethylamino]-3-(3-methyl-4-methylthiophenoxy)propan-2-ol, melting point 139°–141° (from acetonitrile),
1-[2-(3-carbamoyl-4-hydroxyphenoxy)ethylamino]-3-(3-methyl-4-methylsulphinylphenoxy)propan-2-ol with double melting point 92° and 140°,
1-[2-(3-carbamoyl-4-hydroxyphenoxy)ethylamino]-3-(3-methyl-1,2,4-thiadiazol-5-yloxy)propan-2-ol, after chromatography on silica gel, as an amorphous powder having a melting point of 132° after sintering.

EXAMPLE 19

3.09 g of 4-(2,3-epoxypropoxy)benzimidazol-2-one and 4.29 g of 5-[2-(benzylamino)ethoxy]salicylamide are refluxed for 3 hours in 80 ml of isopropanol. The solvent is then removed under reduced pressure. The crude N-[2-(4-hydroxy-3-carbamoylphenoxy)ethyl]-N-[3-(2-oxobenzimidazol-4-yloxy)-2-hydroxypropyl]-N-benzylamine remaining is dissolved in 80 ml of methanol, 3 ml of a 5N methanolic hydrogen chloride solution are added thereto, and the whole is than shaken with the addition of 0.8 g of Pd/C-catalyst (5%) in a hydrogenating apparatus under a hydrogen atmosphere. When the hydrogen absorption corresponding to the calculated amount has ceased, the catalyst is filtered off, and the filtrate is concentrated under reduced pressure. As the concentrate cools, 4-[3-[2-(3-carbamoyl-4-hydroxyphenoxy)ethylamino]-2-hydroxypropoxy]benzimidazol-2-one hydrochloride crystallises, melting point 148°–152° (after recrystallisation from methanol).

EXAMPLE 20

By catalytic debenzylation of 1-[N-[2-(4-carbamoyl-3-hydroxyphenoxy)ethyl-benzylamino]-3-[4-(2-methoxyethoxy)phenoxy]propan-2-ol, analogously to Example 1 there is obtained 1-[2-(4-carbamoyl-3-hydroxyphenoxy)ethylamino]-3-[4-(2-methoxyethoxy)phenoxy]propan-2-ol having a melting point of 151°–152° (from methanol).

The starting material is prepared as follows:
(20a) 16.2 g of 2,3-dihydro-2,2-dimethyl-7-hydroxy-4H-1,3-benzoxazin-4-one are reacted analogously to Example (3a) with 84 ml of 1,2-dibromoethane and yield 2,3-dihydro-2,2-dimethyl-7-(2-bromoethoxy)-4H-1,3-benzoxazin-4-one having a melting point of 156°–158° (from isopropanol).

(20b) 53 g of 2,3-dihydro-2,2-dimethyl-7-(2-bromoethoxy)-4H-1,3-benzoxazin-4-one and 94 g of benzylamine are boiled for 3 hours whilst stirring. The reaction mixture is rendered alkaline with concentrated ammonia, and the organic phase is concentrated by evaporation at a maximum temperature of 50°.

The 4-[2-(benzylamino)ethoxy]salicylamide obtained in this manner forms an oil, the hydrochloride of which melts at 252°–254° (from methanol).

(20c) Analogously to Example (4a), using 4-[2-(benzylamino)ethoxy]salicylamide, 1-[N-[2-(4-carbamoyl-3-hydroxyphenoxy)ethyl]benzylamino]-3-[4-(2-methoxyethoxy)phenoxy]propan-2-ol is obtained as an oil which is debenzylated in its crude state.

EXAMPLE 21

Analogously to Example 8, by debenzylation of crude 1-[N-[2-(3-carbamoyl-4-hydroxyphenoxy)ethyl]-benzylamino]-3-(4-benzyloxyphenoxy)propan-2-ol, 1-[2-(3-carbamoyl-4-hydroxyphenoxy)ethylamino]-3-(4-hydroxyphenoxy)propan-2-ol having a melting point of 130°–131° (from isopropanol), and, using the 4-carbamoyl-3-hydroxy isomer, 1-(2-(4-carbamoyl-3-hydroxyphenoxy)ethylamino]-3-(4-hydroxyphenoxy)propan-2-ol having a melting point of 148°–151° (from methanol) are obtained, the hydrochloride salt of which melts at 224°–226°.

(21a) The starting materials may be obtained by reacting benzyl-(4-(2,3-epoxypropoxy)phenyl]ether with 5- or 4-[2-(benzylamino)ethoxy]salicylamide respectively analogously to Example 8b.

EXAMPLE 22

Analogously to Example 13, using 6-(2-bromoethoxy)salicylamide, 1-[2-(2-carbamoyl-3-hydroxyphenoxy)ethylamino]-3-[4-(2-methoxyethoxy)phenoxy]propan-2-ol is obtained; melting point 176°–179° (from methanol).

(22a) The starting material may be prepared as follows:
A mixture of 23.0 g of 2,6-dihydroxybenzamide, 20.7 g of potassium carbonate and 28.2 g of 1,2-dibromoethane is refluxed, whilst stirring, for 2–3 hours in 300 ml of acetonitrile. The reaction mixture is filtered whilst still warm, the filtrate concentrated by evaporation and the residue recrystallised from a little methanol. 6-(2-Bromoethoxy)salicylamide having a melting point of 120°–121° is obtained.

EXAMPLE 23

The solution of 2.24 g of 5-(2-amino-2-methylpropoxy)salicylamide in 30 ml of dioxan is refluxed for 7 hours after the addition of 2.3 g of 2-(2,3-epoxypropoxy)benzonitrile, and then concentrated by evaporation. The residue is divided between 10 ml of 2N hydrochloric acid and 100 ml of ethyl acetate. The acidic aqueous phase is rendered alkaline with concentrated ammonia solution, the base is extracted with ethyl acetate and the solvent is evaporated off, whereupon an oil is obtained from which, by crystallisation from isopropanol and recrystallisation from ethyl acetate, 1-[2-(3-carbamoyl-4-hydroxyphenoxy)-1,1-dimethylethylamino]-3-(2-cyanophenoxy)propan-2-ol having a melting point of 125°–126° is obtained.

The starting material may be obtained as follows:

(23a) A mixture of 84.3 g of 2,3-dihydro-2,2-dimethyl-6-hydroxy-4H-1,3-benzoxazin-4-one, 144.2 g of methanesulphonic acid (2-methyl-2-nitropropyl) ester and 121 g of dry potassium carbonate in 440 ml of diethylene glycol dimethyl ether is stirred for 9 hours in a bath at approximately 150°. The reaction mixture is cooled, poured into 4000 ml of water and extracted with 3000 ml of ethyl acetate. The oil obtained by concentrating the organic phase by evaporation is dissolved in 250 ml of dioxan, and approximately 750 ml of 2N hydrochloric acid are added until the reaction mixture turns acidic. The solution is maintained at 80°–100° for one and a half hours, then concentrated to half the volume under reduced pressure and extracted 3 times with 500 ml of ethyl acetate each time. The combined organic phases are washed with 200 ml of water, then with saturated sodium carbonate solution and finally with saturated sodium chloride solution, dried over magnesium sulphate and concentrated by evaporation. The dark brown oil obtained in this manner is chromatographed on 500 g of silica gel. By elution with ether crystalline 5-(2-methyl-2-nitropropoxy)salicylamide having a melting point of 145°–148° is obtained.

(23b) 11.5 g 5-(2-methyl-2-nitropropoxy)salicylamide are hydrogenated in 150 ml of methanol at 40°–50° and 80 bar over 5 g of Raney nickel until hydrogen absorption ceases. By filtration and concentration of the filtrate by evaporation, crude 5-(2-amino-2-methylpropoxy)salicylamide is obtained, which, after standing for a relatively long period, crystallises from isopropanol and melts at 115°–117°.

EXAMPLE 24

A mixture of 50 ml of dioxan and 500 ml of concentrated ammonia solution is added to 21.5 g of 1-[2-(3-carbamoyl-4-hydroxyphenoxy)-1-methylethylamino]-3-(3-hydroxy-4-methoxycarbonylphenoxy)propan-2-ol. The reaction mixture is stirred for 1–2 hours, and as soon as it is homogeneous, left to stand for 3 days at 20°–30°. By concentration by evaporation, 20 g of crude, crystalline 1-(4-carbamoyl-3-hydroxyphenoxy)-3-[2-(3-carbamoyl-4-hydroxyphenoxy)-1-methylethylamino]propan-2-ol is obtained as a diastereoisomeric mixture having a melting point of 180°–190°. A hydrochloride is formed which melts at 238°–243° (from ethanol/methanol).

The starting material may be prepared in the following manner:

(24a) By refluxing 34 g of 2,4-dihydroxybenzoic acid methyl ester with 185 g of epichlorohydrin and 35 g of potassium carbonate for 2 to 3 hours, and chromatographing the crude product on 100 g of silica gel (elution with toluene), 4-(2,3-epoxypropoxy)salicylic acid methyl ester having a melting point of 53°–55° is obtained.

(24b) After 40 hours' boiling and working up analogously to Example (4a), 22.4 g of 4-(2,3-epoxypropoxy)salicylic acid methyl ester and 30 g of 5-(2-benzylaminopropoxy)salicylamide in 200 ml of isopropanol yield crude 1-[N-[2-(3-carbamoyl-4-hydroxyphenoxy)-1-methylethyl]benzylamino]-3-(3-hydroxy-4-methoxycarbonylphenoxy)propan-2-ol as a light-coloured foam which is further processed as a crude product.

(24c) A solution of 46 g of 1-[N-[2-(3-carbamoyl-4-hydroxyphenoxy)-1-methylethyl]benzylamino]-3-(3-hydroxy-4-methoxycarbonylphenoxy)propan-2-ol in 500 ml of methanol is hydrogenated with the addition of 5 g of Pd/C-catalyst (5%) under normal conditions until 1 equivalent of hydrogen has been absorbed. The product, which has partially crystallised out, is dissolved in about 2000 ml of hot methanol and the catalyst is filtered off. By concentrating the filtrate, 1-[2-(3-carbamoyl-4-hydroxyphenoxy)-1-methylethylamino]-3-(3-hydroxy-4-methoxycarbonylphenoxy)propan-2-ol having a melting point of 168°–172° is obtained as a diastereoisomeric mixture.

EXAMPLE 5

5.2 g of crude 1-[N-[2-(3-carbamoyl-2-hydroxyphenoxy)ethyl]benzylamino]-3-[4-(2-methoxyethoxy)phenoxy]propan-2-ol are hydrogenated and worked up analogously to Example 4. After recrystallisation from isopropanol, 1-[2-(3-carbamoyl-2-hydroxyphenoxy)ethylamino]-3-[4-(2-methoxyethoxy)phenoxy]propan-2-ol having a melting point of 125°–129° is obtained.

The starting material is prepared as follows:

(25a) 2,3-dihydroxybenzoic acid methyl ester is reacted in the presence of potassium carbonate in acetonitrile with 1.1 equivalents of 1-dibenzylamino-2-chloroethane for 18 hours at 82°. The crude 3-(2-dibenzylaminoethoxy)salicyclic acid methyl ester obtained after working up is put to further use without further purification.

(25b) The compound obtained in accordance with example (25a) is dissolved in methanol and, after the addition of palladium-on-carbon catalyst, is hydrogenated until 1.1 equivalents of hydrogen have been absorbed. The catalyst is filtered off, the solvent evaporated off, the residue taken up in ethyl acetate, the organic phase washed with water and concentrated by evaporation, after which the crude 3-(2-benzylaminoethoxy)salicylic acid methyl ester is obtained as a honey-coloured oil.

(25c) The product obtained in accordance with Example (25b) is stirred with 10 times the amount by weight of concentrated ammonia, and when dissolution has occurred, is left to stand for 4 to 5 days at room temperature. The solution is then concentrated by evaporation, the residue is divided between water and ethyl acetate, the organic phase is dried over magnesium sulphate and concentrated by evaporation, after which 3-(2-benzylaminoethoxy)salicylamide is obtained as a yellowish oil.

(25d) By reacting 2.5 g of 1-(2,3-epoxypropoxy)-4-(2-methoxyethoxy)benzene with 2.9 g of crude 3-(2-benzylaminoethoxy)salicylamide obtained according to Example (25c), analogously to Example (4a), 1-[N-[2-(3-carbamoyl-2-hydroxyphenoxy)ethyl]benzylamino]-3-[4-(2-methoxyethoxy)phenoxy]propan-2-ol is obtained as an oil which is further processed in this state

EXAMPLE 26

A solution of 2.5 g of 1-amino-3-[4-(2-methoxyethoxy)phenoxy]propan-2-ol and 2.23 g of (2,3-dihydro-2,2-dimethyl-4H-1,3-benzoxazin-4-on-6-yloxy)acetaldehyde in 20 ml of ethanol is refluxed for 3 hours. After cooling, 0.8 g of sodium borohydride is added in portions, whilst stirring, and stirring is continued for a further 3–4 hours at room temperature.

By adding 2N hydrochloric acid, the excess sodium borohydride is decomposed, the solution is then concentrated by evaporation, the residue rendered alkaline with ammonia solution and extracted 3 times with 300 ml of ethyl acetate each time. By concentrating by evaporation the combined ethyl acetate solutions dried over magnesium sulphate, a brown residue is obtained, from which, by repeated recrystallisation from isopropanol, 1-[2-(3-carbamoyl-4-hydroxyphenoxy)ethylamino]-3-[4-(2-methoxyethoxy)phenoxy]propan-2-ol having a melting point of 157°–158° is obtained.

The starting material is prepared as follows:

(26a) A solution of 9.65 g of 2,3-dihydro-2,2-dimethyl-6-hydroxy-4H-1,3-benzoxazin-4-one and 9.1 g of allyl bromide in 150 ml of acetonitrile is refluxed for 5 hours, whilst stirring, with the addition of 10.3 g of dry potassium carbonate. The reaction mixture is filtered whilst warm, the filtrate is concentrated by evaporation and the remaining crystals are suction-filtered after trituration with ether. The crude 2,3-dihydro-2,2-dimethyl-6-(1-propen-3-yloxy)-4H-1,3-benzoxazin-4-one obtained in this manner melts at 137°–138°.

(26b) Approximately 20 mg of osmium tetroxide are added to a solution of 4.7 g of 2,3-dihydro-2,2-dimethyl-6-(1-propen-3-yloxy)-4H-1,3-benzoxazin-4-one in a mixture of 50 ml of dioxan and 15 ml of water whilst stirring. After 15 minutes 8.6 g of sodium metaperiodate are added in portions, the temperature rising to 45°. After 2 hours the reaction mixture is filtered, the filtrate concentrated by evaporation and the residue divided between 20 ml of water and 200 ml of ethyl acetate. The organic phase is separated off, dried over sodium sulphate and concentrated by evaporation, and the resulting oil is chromatographed on 100 g of silica gel. By elution with ethyl acetate and concentration by evaporation, (2,3-dihydro-2,2-dimethyl-4H-1,3-benzoxazin-4-on-6-yloxy)acetaldehyde having a melting point of 153°–163° is obtained.

EXAMPLE 27

After the addition of 0.2 g of palladium-on-carbon catalyst, a solution of 4.1 g of 1-(2-allyloxyphenoxy)-3-[2-(3-carbamoyl-4-hydroxyphenoxy)ethylamino]propan-2-ol in 100 ml of methanol is hydrogenated under normal conditions until 1 equivalent of hydrogen has been absorbed. By filtration and concentration of the solution by evaporation, colourless crystals are obtained which melt at 142°–143° after recrystallisation from methanol and consist of 1-[2-(3-carbamoyl-4-hydroxyphenoxy)ethylamino]-3-(2-propoxyphenoxy)propan-2-ol.

EXAMPLE 28

Analogously to Example 8, using 1-[N-[2-(3-carbamoyl-4-hydroxyphenoxy)ethyl]benzylamino]-3-(2-benzyloxyphenoxy)propan-2-ol as starting material, 1-[2-(3-carbamoyl-4-hydroxyphenoxy)ethylamino]-3-(2-hydroxyphenoxy)propan-2-ol is obtained which forms a neutral fumarate having a melting point of 178°–180° (from ethanol).

The starting material can be obtained analogously to Example (8b) from benzyl-[2-(2,3-epoxypropoxy)-phenyl]ether and 5-[2-(benzylamino)ethoxy]salicylamide.

EXAMPLE 29

Analogously to Example 4,
(a) from 1-[N-[2-(3-carbamoyl-4-hydroxyphenoxy)ethyl]benzylamino]-3-(3-carbamoyl-4-hydroxyphenoxy)propan-2-ol there is obtained 1-[2-(3-carbamoyl-4-hydroxyphenoxy)ethylamino]-3-(3-carbamoyl-4-hydroxyphenoxy)propan-2-ol, melting point 212°–215°, (from methanol);
(b) from 1-[N-[2-(3-carbamoyl-4-hydroxyphenoxy)ethyl]benzylamino]-3-[4-(2-oxopropoxy)phenoxy]propan-2-ol there is obtained 1-[2-(3-carbamoyl-4-hydroxyphenoxy)ethylamino]-3-[4-(2-oxopropoxy)-phenoxy]propan-2-ol, melting point 118°–120° (from acetonitrile).

EXAMPLE 30

Analogously to Example 17, the following compounds are obtained using the correspondingly substituted epoxides:
1-[2-(3-carbamoyl-4-hydroxyphenoxy)ethylamino]-3-[4-(2-acetamidoethyl)phenoxy]propan-2-ol; melting point of the hydrochloride 223°–224° (from methanol),
1-[2-(3-carbamoyl-4-hydroxyphenoxy)ethylamino]-3-(4-acetamidomethylphenoxy)propan-2-ol, melting point 173°–176° (from Methyl Cellosolve),
1-[2-(3-carbamoyl-4-hydroxyphenoxy)ethylamino]-3-(4-carbamoylmethylphenoxy)propan-2-ol, melting point 181°–182°, (from dimethylformamide/water).

EXAMPLE 31

A solution of 25 g of crude 1-[N-[4-(3-carbamoyl-4-hydroxyphenoxy)butyl]benzylamino]-3-[4-(2-methoxyethoxy)phenoxy]propan-2-ol in 250 ml of methanol is hydrogenated and worked up analogously to Example 4. The resulting crystalline crude product is recrystallised from isopropanol and yields 1-[4-(3-carbamoyl-4-hydroxyphenoxy)butylamino]-3-[4-(2-methoxyethoxy)-phenoxy]propan-2-ol having a melting point of 122°–124°.

The starting material is prepared as follows:
(31a) A suspension of 96.5 g of 2,3-dihydro-2,2-dimethyl-6-hydroxy-4H-1,3-benzoxazin-4-one and 76 g of potassium carbonate in 300 ml of 1,4-dibromobutane is stirred for 5 hours in a bath at 120°–130°. The reaction mixture is filtered and the excess 1,4-dibromobutane is distilled off at about 1 torr. The crystalline residue is triturated with ether and suction-filtered. In this manner crude 2,3-dihydro-2,2-dimethyl-6-(4-bromobutoxy)-4H-1,3-benzoxazin-4-one having a melting point of 139°–142°, which is sufficiently pure for further reaction, is obtained.

(31b) A mixture of 65.6 g of 2,3-dihydro-2,2-dimethyl-6-(4-bromobutoxy)-4H-1,3-benzoxazin-4-one, 85 g of benzylamine and 100 ml of water is heated at 110°-120° for 1 hour, whilst stirring. Whilst cooling with ice, the reaction mixture is then acidified with concentrated hydrochloric acid, a salt mixture of 5-(4-benzylaminoethoxy)salicylamide crystallising out after a few hours. The base liberated therefrom by means of 20% ammonia is extracted with ethyl acetate and the organic phase is evaporated off. The residue forms an oil which crystallises gradually, (melting point 103°-106°, sinters at a temperature of 86° and above).

(31c) A solution of 15.7 g of the compound obtained according to Example 23b and 13.4 g of 1-(2,3-epoxypropoxy)-4-(2-methoxyethoxy)benzene is reacted analogously to Example 4a) to give 1-[N-[4-(3-carbamoyl-4-hydroxyphenoxy)butyl]benzylamino]-3-[4-(2-methoxyethoxy)phenoxy]propan-2-ol and is further processed in this state.

EXAMPLE 32

A mixture of 8.4 g of 1-[2-(3-carbamoyl-4-hydroxyphenoxy)ethylamino]-3-[4-(2-methoxyethoxy)phenoxy]propan-2-ol and 30 ml of n-butylamine is heated in a rotating closed vessel for 17 hours at 160°-170°. After evaporating off the butylamine, a crystalline residue is left which is recrystallised from methanol and yields 1-[2-(3-N-n-butylcarbamoyl-4-hydroxyphenoxy)ethylamino]-3-[4-(2-methoxyethoxy)phenoxy]propan-2-ol having a melting point of 118°-119°.

EXAMPLE 33

A mixture of 8.1 g of 1-[2-(3-carbamoyl-4-hydroxyphenoxy)ethylamino]-3-(2-propoxyphenoxy)propan-2-ol and 50 ml of a 33% solution of methylamine in ethanol is reacted analogously to Example 32 in a closed vessel. By concentrating the resulting solution by evaporation, an oil is obtained which is neutralised by adding a 5N solution of hydrochloric acid in methanol. After adding ether until the solution starts tuning turbid, 1-[2-[3-(N-methylcarbamoyl)-4-hydroxyphenoxy]ethylamino]-3-(2-propoxyphenoxy)propan-2-ol gradually crystallises out as a hydrochloride having a melting point of 114°-116°.

In an analogous manner, using piperidine 1-[2-[3-(N-piperidinocarbonyl)-4-hydroxyphenyl]ethylamino]-3-(2-propoxyphenoxy)propan-2-ol is obtained as a viscous oil, the IR- and $^1$H-NMR-spectra of which are in concordance with the assumed structure and the Rf-value of which is 0.70 according to thin-layer chromatography on silicagel using a mixture of ethylacetate-ethanol-conc. ammonia 24:12:4 as the eluent.

EXAMPLE 34

7.3 g of 2-(2,3-epoxypropoxy)benzonitrile are added to a solution of 6.7 g of 5-(4-aminobutyl)salicylamide in 60 ml of dimethyl sulphoxide and the mixture is stirred for 1 hour in a bath at 90°. The reaction mixture is poured into 300 ml of water and extracted twice with 200 ml of ethyl acetate each time. Working up analogously to Example 23 yields crude 1-[4-(3-carbamoyl-4-hydroxyphenoxy)butylamino]-3-(2-cyanophenoxy)propan-2-ol as a viscous oil, the IR- and $^1$H-NMR-spectra of which are in concordance with the assumed structure and the Rf-value of which is 0,51 according to thin-layer chromatography on silicagel using a mixture of ethylacetate-ethanol-conc. ammonia 24:12:4 as the eluent.

5-(4-Aminobutoxy)salicylamide needed as starting material is obtained by catalytic debenzylation of 5-[4-(benzylamino)butoxy]salicylamide in methanol using a palladium-on-carbon catalyst (5%), melting point 78°-81° (from ethanol).

EXAMPLE 35

A solution of 3.5 g of 1-[2-(3-cyano-4-hydroxyphenoxy)ethylamino]-3-[4-(2-methoxyethoxy)phenoxy]propan-2-ol in a mixture of 15 ml of concentrated hydrochloric acid and 20 ml of dioxan is stirred for 15 hours at 20°-25°. The reaction mixture is then concentrated by evaporation and rendered alkaline with 10% aqueous ammonia solution. The crude 1-[2-(3-carbamoyl-4-hydroxyphenoxy)ethylamino]-3-[4-(2-methoxyethoxy)phenoxy]propan-2-ol which is precipitated after standing for a few hours is filtered off and recrystallised from a mixture of dioxan/methanol (1:1). Melting point 157°-158°.

1-[2-(3-cyano-4-hydroxyphenoxy)ethylamino]-3-[4-(2-methoxyethoxy)phenoxy]propan-2-ol needed as starting material is obtainable in a manner analogous to the method described in Example 13 from 1-[4-(2-methoxyethoxy)phenoxy]-3-aminopropan-2-ol and 5-(2-bromoethoxy)-2-hydroxybenzonitrile. The crude product obtained after working up is put to further use in this state.

EXAMPLE 36

Tablets containing 20 mg of active substance are manufactured in the following composition in the customary manner.

| Composition: | |
|---|---|
| 1-[2-(3-carbamoyl-4-hydroxyphenoxy)-ethylamino]-3-[4-(2-methoxyethoxy)-phenoxy]propan-2-ol | 20 mg |
| wheat starch | 60 mg |
| lactose | 50 mg |
| colloidal silica | 5 mg |
| talc | 9 mg |
| magnesium stearate | 1 mg |
| | 145 mg |

Manufacture:

1-[2-(3-carbamoyl-4-hydroxyphenoxy)ethylamino]-3-[4-(2-methoxyethoxy)phenoxy]propan-2-ol is mixed with part of the wheat starch, with the lactose and colloidal silica and the mixture is pressed through a sieve. A further portion of the wheat starch is made into a paste using a water bath with 5 times the amount of water and the powder mixture is kneaded with this paste until a slightly plastic composition has formed.

The plastic composition is pressed through a sieve having a mesh width of approximately 3 mm, dried, and the resulting dry granulate is again pressed through a sieve. The remaining wheat starch, the talc and magnesium stearate are then admixed and the mixture is compressed to form tablets of 145 mg weight having a breaking groove.

EXAMPLE 37

Tablets containing 1 mg of active substance are manufactured in the following composition in the customary manner:

| Composition: | |
|---|---|
| 1-(4-hydroxyphenoxy)-3-[2-(3-carbamoyl-4-hydroxyphenoxy)-1-methylethylamino]propan-2-ol | 1 mg |
| wheat starch | 60 mg |
| lactose | 50 mg |
| colloidal silica | 5 mg |
| talc | 9 mg |
| magnesium stearate | 1 mg |
| | 126 mg |

Manufacture:

1-(4-Hydroxyphenoxy)-3-[2-(3-carbamoyl-4-hydroxyphenoxy)-1-methylethylamino]propan-2-ol is mixed with part of the wheat starch, with the lactose and colloidal silica and the mixture is pressed through a sieve. A further portion of the wheat starch is made into a paste using a water bath with 5 times the amount of water, and the powder mixture is kneaded with this paste until a slightly plastic composition has formed.

The plastic composition is pressed through a sieve having a mesh width of approximately 3 mm, dried, and the resulting dry granulate is again pressed through a sieve. The remaining wheat starch, the talc and magnesium stearate are then admixed, and the mixture is compressed to form tablets of 145 mg weight having a breaking groove.

EXAMPLE 38

Capsules containing 10 mg of active substance are manufactured in the customary manner as follows:

| Composition: | |
|---|---|
| 1-(2-allyloxyphenoxy)-3-[2-(3-carbamoyl-4-hydroxyphenoxy)ethylamino]propan-2-ol | 2500 mg |
| talc | 200 mg |
| colloidal silica | 50 mg |

Manufacture:

The active substance is intimately mixed with the talc and colloidal silica, the mixture is pressed through a sieve having a mesh width of 0.5 mm, and introduced in 11 mg portions into hard gelatin capsules of suitable size.

EXAMPLE 39

A sterile solution of 5.0 g of 1-[2-(3-carbamoyl-4-hydroxyphenoxy)ethylamino]-3-[4-(2-methoxyethoxy)phenoxy]propan-2-ol methane sulphonate in 500 ml of distilled water is introduced into 5 ml ampoules which contain 5 mg of active substance in 5 ml of solution.

EXAMPLE 40

3.62 g of 1-[2-(3-carbamoyl-4-hydroxyphenoxy)ethylamino]-3-(4-hydroxyphenoxy)propan-2-ol are dissolved, with the addition of 100.0 ml of 0.10N hydrochloric acid, in 18000 ml of distilled water to a volume of 18100 ml. The sterilised solution is introduced into 5.0 ml ampoules containing 1 mg of active substance.

EXAMPLE 41

Instead of the compounds used as the active substances in Examples 36 to 40, the following compounds of the formula I, or the pharmaceutically acceptable non-toxic acid addition salts thereof, may also be used as active substances in tablets, draëes, capsules, ampoule solutions etc.:

1-[2-(3-carbamoyl-4-hydroxyphenoxy)-1-methylethylamino]-3-[4-(2-methoxyethoxy)phenoxy]propan-2-ol, 1-[2-(4-carbamoyl-3-hydroxyphenoxy)-1-methylethylamino]-3-[4-(2-methoxyethoxy)phenoxy]propan-2-ol, 1-[2-(3-carbamoyl-4-hydroxyphenoxy)ethylamino]-3-[2-[N-(2-hydroxyethyl)carbamoylmethoxy]phenoxy]propan-2-ol, 1-[2-(3-carbamoyl-4-hydroxyphenoxy)ethylamino]-3-phenoxypropan-2-ol, 1-[2-(3-carbamoyl-4-hydroxyphenoxy)ethylamino]-3-[4-[2-(methoxycarbonyl)ethoxy]phenoxy]propan-2-ol, 1-(4-acetamidophenoxy)-3-[2-(3-carbamoyl-4-hydroxyphenoxy)ethylamino]propan-2-ol, 1-[2-(3-carbamoyl-4-hydroxyphenoxy)ethylamino]-3-(2-methylphenoxy)propan-2-ol, 1-[2-(3-carbamoyl-4-hydroxyphenoxy)ethylamino]-3-(3-methylphenoxy)propan-2-ol, 1-[2-(3-carbamoyl-4-hydroxyphenoxy)ethylamino]-3-(2-methylindol-4-yloxy)propan-2-ol, 1-[2-(3-carbamoyl-4-hydroxyphenoxy)ethylamino]-3-(trifluoromethylphenoxy)propan-2-ol, 1-(2-acetylphenoxy)-3-[2-(3-carbamoyl-4-hydroxyphenoxy)ethylamino]propan-2-ol, 1-[4-[2-(acetamido)ethoxy]phenoxy]-3-[2-(3-carbamoyl-4-hydroxyphenoxy)ethylamino]propan-2-ol, 1-[2-(3-carbamoyl-4-hydroxyphenoxy)ethylamino]-3-(3-methylpyridin-2-yloxy)propan-2-ol, 5-[3-[2-(3-carbamoyl-4-hydroxyphenoxy)ethylamino]-2-hydroxypropoxy]-1,2,3,4-tetrahydro-2,3-cis-naphthalene diol, 4-[2-hydroxy-3-[(3-carbamoyl-4-hydroxyphenoxy)ethylamino]propoxy]phenylacetamide, 4-[2-hydroxy-3-[(3-carbamoyl-4-hydroxyphenoxy)ethylamino]propoxy]phenoxyacetamide, N-[4-[2-hydroxy-3-[(3-carbamoyl-4-hydroxyphenoxy)ethylamino]propoxy]phenyl]-N',N'-dimethyl urea, 1-(4-butyroylamino-2-acetylphenoxy)-3-[2-(3-carbamoyl-4-hydroxyphenoxy)ethylamino]propan-2-ol, 1-[2-(3-carbamoyl-4-hydroxyphenoxy)ethylamino]-3-(2-methoxyphenoxy)propan-2-ol, 1-[2-(3-carbamoyl-4-hydroxyphenoxy)ethylamino]-3-(2,3-dimethylphenoxy)propan-2-ol, 1-[2-(3-carbamoyl-4-hydroxyphenoxy)ethylamino]-3-[3-(2-methoxyethoxy)phenoxy]propan-2-ol, 1-[2-(3-carbamoyl-4-hydroxyphenoxy)ethylamino]-3-[2-(pyrrol-1-yl)phenoxy]propan-2-ol, 1-[2-(3-carbamoyl-4-hydroxyphenoxy)ethylamino]-3-(3-methyl-4-methylsulphonylphenoxy)propan-2-ol, 1-[2-(3-carbamoyl-4-hydroxyphenoxy)ethylamino]-3-(1-naphthyloxy)propan-2-ol, 5-[3-[2-(4-carbamoyl-3-hydroxyphenoxy)-1-methylethylamino]-2-hydroxypropoxy]-3,4-dihydro-2(1H)-quinolinone, 1-[3-(3-carbamoyl-4-hydroxyphenyl)propylamino]-3-[4-(2-methoxyethoxy)phenoxy]propan-2-ol, 1-[2-(3-carbamoyl-4-hydroxyphenoxy)-1-methylethylamino]-3-(4-methylcarbamoylphenoxy)propan-2-ol, 1-[2-(3-carbamoyl-4-hydroxyphenoxy)-1-methylethylamino]-3-[4-(2-methoxyethyl)phenoxy]propan-2-ol, 1-(2-allyloxyphenoxy)-3-[2-(3-carbamoyl-4-hydroxyphenoxy)-1-methylethylamino]propan-2-ol, 1-[2-(3-carbamoyl-4-hydroxyphenoxy)ethylamino]-3-(2-cyanophenoxy)propan-2-ol, 1-[2-(3-carbamoyl-4-hydroxyphenoxy)ethylamino]-3-[2-(prop-2-ynyloxy)phenoxy]propan-2-ol, 1-[2-(3-carbamoyl-4-hydroxyphenoxy)ethylamino]-3-[4-(2-methylthioethoxy)phenoxy]propan-2-ol, 1-[2-(3-carbamoyl-4-hydroxyphenoxy)ethylamino]-3-[2-allylphenoxy]propan-2-ol, 1-[2-(3-carbamoyl-4-hydroxyphenoxy)-1-methylethylamino]-3-[4-(carbamoylmethoxy)phenoxy]propan-2-ol, 1-[2-(3-carbamoyl-4-hydroxyphenoxy)ethylamino]-3-[2-[N'-(hydroxyethyl)ureidomethyl]phenoxy]propan-2-ol, 1-[2-(3-carbamoyl-4-hydroxyphenoxy)ethylamino]-3-[2-(prop-2-nyloxy)phenoxy]propan-2-ol, 1-[2-(3-carbamoyl-4-hydroxyphenoxy)ethylamino]-3-(2-cyanophenoxy)propan-2-ol, 1-[2-(3- carbamoyl-4-hydroxyphenoxy)ethylamino]-3-(2-chlorophenoxy)propan-2-ol, 1-[2-(3-carbamoyl-4-hydroxyphenoxy)ethylamino]-3-[4-(2-methylthioethoxy)phenoxy]propan-2-ol, 1-[2-(3-carbamoyl-4-hydroxyphenoxy)ethylamino]-3-(methyl-4-methylthiophenoxy)propan-2-ol, 1-[2-(3-carbamoyl-4-hydroxyphenoxy)ethylamino]-3-(3-methyl-4-methylsulphinylphenoxy)-propan-2-ol, 1- [2-(3-carbamoyl-4-hydroxyphenoxy)ethylamino]-3-(3-methyl-1,2,4-thiadiazol-5-yloxy)propan-2-ol, 1-[3-[2-(3-carbamoyl-4-hydroxypnenoxy)ethylamino]-2-hydroxypropoxy]benzimidazol-2-one hydrochloride, 1-[2-(4-carbamoyl-3-hydroxyphenoxy)ethylamino]-3-[4-(2-methoxyethoxy)phenoxy]propan-2-ol, 1-[2-(2-carbamoyl-3-hydroxyphenoxy)ethylamino]-3-[4-(2-methoxyethoxy)phenoxy]propan-2-ol, 1-[2-(3-carbamoyl-4-hydroxyphenoxy)-1,1-dimethylethylamino]-3-[4-(methylcarbamoyl)phenoxy]propan-2-ol, 1-(4-carbamoyl-3-hydroxyphenoxy)-3-[2-(3-carbamoyl-4-hydroxyphenoxy)-1-methylethylamino]propan-2-ol as a diastereoisomeric mixture,1-[2-(3-carbamoyl-2-hydroxyphenoxy)ethylamino]-3-[4-(2-methoxyethoxy)-phenoxy]propan-2-ol, 1-[2-(3-carbamoyl-4-hydroxyphenoxy)ethylamino]-3-(2-propoxyphenoxy)propan-2-ol, 1-[2-(3-carbamoyl-4-hydroxyphenoxy)ethylamino]-3-(2-hydroxyphenoxy)propan-2-ol, 1-[2-(3-carbamoyl-4-hydroxyphenoxy)ethylamino]-3-(3-carbamoyl-4-hydroxyphenoxy)propan-2-ol, 1-[2-(3-carbamoyl-4-hydroxyphenoxy)ethylamino]-3-(2-carbamoylphenoxy)propan-2-ol, 1-[2-(3-carbamoyl-4-hydroxyphenoxy)ethylamino]-3-[4-(2-oxopropoxy)phenoxy]propan-2-ol, 1-[2-(3-carbamoyl-4-hydroxyphenoxy)ethylamino[4-3-[-(2-acetamidoethyl)phenoxy]propan-2-ol, 1-[2-(3-carbamoyl-4-hydroxyphenoxy)ethylamino]-3-[4-(acetamidomethyl)phenoxy]propan-2-ol, 1-[2-(3-carbamoyl-4-hydroxyphenoxy)ethylamino]-3-(4-carbamoylmethylphenoxy)propan-2-ol, 1-[4-(3-carbamoyl-4-hydroxyphenoxy)butylamino]-3-[4-(2-methoxyethoxy)phenoxy]propan-2-ol, 1[2-[3-(N-n-butylcarbamoyl)-4-hydroxyphenoxy]ethylamino]-3-[4-(2-methoxyethoxy)phenoxy]propan-2-ol, 1-[2-[3-(N-methylcarbamoyl)-4-hydroxyphenoxy]ethylamino]-3-(2-propoxyphenoxy)-propan-2-ol, 1-[4-(3-carbamoyl-4-hydroxyphenoxy)-butylamino]-3-(2-cyanophenoxy)propan-2-ol, 1-[2-(3-carbamoyl-4-hydroxyphenoxy)ethylamino]-3-[2-(2-methoxyethoxy)phenoxy]propan-2-ol, 1-(2-carbamoyl-phenoxy)-3-[2-(3-carbamoyl-4-hydroxyphenoxy)-ethylamino]propan-2-ol, 1-[2-(4-carbamoyl-3-hydroxyphenoxy)ethylamino]-3-(4-hydroxyphenoxy)propan-2-ol, 1-[2-(3-carbamoyl-4-hydroxyphenoxy)-ethylamino]-3-[2-(2,3-dihydroxypropyl)-phenoxy]-2-propanol, 1-[2-(4-carbamoyl-3-hydroxyphenoxy)-1-methylethylamino]-2-(methansulphonylaminophenoxy)-2-propanol, 1[2-(3-carbamoyl-4-hydroxyphenoxy)ethylamino]-3-[4-[2-(cyclopropylmethoxy)-ethyl]-phenoxy]-2-propanol, 1-[2-(3-carbamoyl-4-hydroxyphenoxy)-ethylamino]-3-(4-methanesulphonylamino-phenoxy)-2-propanol, 1-[2-(3-carbamoyl-4-hydroxyphenoxy)-1-methyl-ethylamino]-3-(4-methanesulphonylamino-phenoxy)-2-propanol, 1-[2-(3-carbamoyl-4-hydroxyphenoxy)-ethylamino]-3-[4-(N-methyl-methanesulphonylamino)phenoxy]-2-propanol or 4-[3-[2-(3-carbamoyl-4-hydroxy-phenoxy)ethylamino]-2-hydroxy-propoxy]-N-methylcinnamic acid amide.

EXAMPLE 42

A solution of 6.9 g of 1-[2-(3-carbamoyl-4-hydroxyphenoxy)-ethylamino]-3-[2-(2,2-dimethyl-dioxolan-4-yl)-methyl]phenoxy]-2-propanol in 165 ml of 0.1N hydrochloric acid is left to stand at 20° for 5 hours. It is then washed twice with ether; the aqueous phase is filtered, and is subsequently concentrated in vacuo with a bath-temperature of 40°. The aqueous solution obtained is lyophilised to yield 1-[2-(3-carbamoyl-4-hydroxy-phenoxy)-ethylamino]-3-[2-(2,3-dihydroxypropyl)-phenoxy]-2-propanol hydrochloride in the form of colourless amorphous powder.

The starting material can be produced in the following manner:

(a) A mixture of 76.8 g of 4-(2-hydroxybenzyl)-2,2-dimethyl-1,3-dioxolane, 248 ml of epichlorohydrin and 69.7 g of potassium carbonate is stirred for 7 hours at a bath-temperature of 130°.

The reaction mixture is filtered, and concentrated in vacuo to dryness. The residue is dissolved in ether; the solution is washed with 2N sodium hydroxide solution and then with water; it is dried over sodium sulfate and subsequently concentrated by evaporation. The resulting crude 4-[2-(2,3-epoxy-propoxy)-benzyl]-2,2-dimethyl-1,3-dioxolane is further processed as such.

(b) A mixture of 17.4 g of the crude compound obtained and 17.1 g of 5-(2-benzylamino-ethoxy)-salicylamide in 60 ml of dimethyl sulfoxide is stirred for 20 hours at a bath-temperature of 80°. The reaction mixture is poured into ice and water, and extracted with ethyl acetate. The organic phase is diluted with ether, and successively washed with 0.1N hydrochloric acid (at pH 4–5) and then with aqueous saturated potassium carbonate solution, and dried over sodium sulfate. Concentration by evaporation leaves an oil, which is chromatographed through silica gel with methylene chloride/methanol. Further processing yields 1-[N-[2-(3-carbamoyl-4-hydroxy-phenoxy)-ethyl]-benzyl-amino]-3-[2-[(2,2-dimethyl-dioxolan-4-yl)-methyl]-phenoxy]-2-propanol as thick oil.

(c) A solution of 23.5 g of the resulting compound in 240 ml of methanol is hydrogenated with the addition of 2.4 g of palladium-on-charcoal catalyst under normal conditions. The reaction product is dissolved in ethyl acetate, and precipitated in crystalline form by the addition of petroleum ether. The crystals are again dissolved in ethyl acetate, and the solution is stirred with 4.5 g of silica gel for ½ hour. Petroleum ether is added portionwise to the filtrated solution to thus obtain 1-[2-(3-carbamoyl-4-hydroxy-phenoxy)-ethylamino]-3-[2-[(2,2-dimethyl-dioxolan-4-yl)-methyl]-phenoxy]-2-propanol, m.p. 91°–93°.

EXAMPLE 43

A solution of 20.0 g of crude 1-[N-[2-(4-carbamoyl-3-hydroxy-phenoxy)-1-methyl-ethyl]-benzylamino]-3-(4-methanesulfonylamino-phenoxy)-2-propanol in 250 ml of methanol is hydrogenated, after the addition of 2.5 g of Pd/C catalyst (5%), under normal conditions until debenzylation is completed (DC control), for which an addition of a further 1.0 g of catalyst is required. The catalyst is filtered off; the filtrate is concentrated by evaporation, and the oil remaining behind is dissolved in a small amount of hot isopropanol. On cooling is obtained crystalline 1-[2-(4-carbamoyl-3-hydroxy-phenoxy)-1-methyl-ethylamino]-3-(4-methanesulfonylamino-phenoxy)-2-propanol, m.p. 147°–150° (diastereoisomeric mixture).

The starting material is obtained in the following manner:

(43a) According to the method described by Irvine et al., Synthesis 1972, 568, 2,4-dihydroxybenzamide is converted, using an excess of acetone, into 2,3-dihydro-2,2-dimethyl-7-hydroxy-4H-1,3-benzoxazin-4-one, m.p. 249°–251°.

(43b) From 168 g of 2,3-dihydro-2,2-dimethyl-7-hydroxy-4H-1,3-benzoxazin-4-one, 305 g of potassium carbonate and 88 ml of chloroacetone in 1.2 liters of acetonitrile is obtained, by boiling for 28 hours and subsequent processing, 2,3-dihydro-2,2-dimethyl-7-(2-oxo-propoxy)-4H-1,3-benzoxazin-4-one, m.p. 160°–162° (from isopropanol).

(43c) A solution of 75 g of crude 2,3-dihydro-2,2-dimethyl-7-(2-oxo-propoxy)-4H-1,3-benzoxazin-4-one and 32 g of benzylamine in 1000 ml of methanol is hydrogenated, with the addition of 0.75 g of conc. sulfuric acid and 1.6 g of a Pt/C catalyst (5%), under normal condition until the absorption of hydrogen has ceased. After removal of the catalyst by filtration and of the solvent by evaporation, the oily residue is distributed between 300 ml of ethyl acetate and 500 ml of 2N hydrochloric acid. There is then isolated from the aqueous phase, by rendering alkaline with concentrated ammonia (ice-cooling) and extracting with ethyl acetate, crude 2,3-dihydro-2,2-dimethyl-7-[(2-benzylamino)propoxy]-4H-1,3-benzoxazin-4-one in the form of oil, which can be further processed in the crude state.

(43d) A mixture of 100 g of crude 2,3-dihydro-2,2-dimethyl-7-[(2-benzylamino)-propoxy]-4H-1,3-benzoxazin-4-one, 100 ml of isopropanol and 100 ml of isopropylamine is refluxed for 1 hour, and then concentrated by evaporation. The oil remaining behind crystallises on trituration with ether. The crystals are filtered off with suction, and washed with a small amount of isopropanol to thus yield 4-[2-(benzylamino)-propoxy]-salicylamide, m.p. 121°–123°.

(43e) A solution of 19.0 g of 4-[2-(benzylamino)-propoxy]salicylamide and 12.4 g of 4-(2,3-epoxypropoxy)-nitrobenzene in 300 ml of isopropanol is refluxed for 20 hours. After the addition of a further 1.2 g of 4-(2,3-epoxypropoxy)nitrobenzene, refluxing is continued for a further 20 hours. The solvent is subsequently partially evaporated off, whereupon 1-[N-[2-(4-carbamoyl-3-hydroxy-phenoxy)-1-methylethyl]-benzylamino]-3-(4-nitrophenoxy)-2-propanol, m.p. 160°–164° (diastereoisomeric mixture) crystallises out.

(43f) A solution of 19.0 g of the resulting compound in 380 ml of dioxane is hydrogenated, with the addition of 18 g of Raney nickel in 4 portions, under normal conditions, until 3 mol-equivalents of hydrogen have been absorbed. After filtration and subsequent concentration by evaporation of the filtrate, there remains behind crude 1-[N-[2-(4-carbamoyl-3-hydroxy-phenoxy)-1-methyl-ethyl]-benzylamino]-3-(4-aminophenoxy)-2-propanol in the form of orange-brown oil, which can be further processed without additional purification.

(43g) 16 g of the compound obtained are dissolved in 90 ml of anhydrous pyridine, and to the solution are added dropwise, with cooling to 5°–10°, 4.4 g of methanesulfonic acid chloride. The reaction mixture is stirred for 4 hours at room temperature; the solvent is then evaporated off, and the residue is distributed between 400 ml of ethyl acetate and 50 ml of water. The organic phase is washed three times with 50 ml of water each time and dried over magnesium sulfate; it is subsequently treated with charcoal, and concentrated by evaporation to yield crude 1-[N-[2-(4-carbamoyl-3-hydroxy-phenoxy)-1-methyl-ethyl]-benzylamino]-3-(4-methanesulfonylamino-phenoxy)-2-propanol in the form of orange-coloured oil, which can be further processed without additional purification.

EXAMPLE 44

A solution of 30 g of crude 1-[N-[2-(3-carbamoyl-4-hydroxy-phenoxy)-ethyl]-benzylamino]-3-[4-[2-(cyclopropylmethoxy)ethyl]-phenoxy]-2-propanol in 600 ml of methanol is hydrogenated, with the addition of 4 g of a Pd/C catalyst (5%), under normal conditions until 1 mol-equivalent of hydrogen has been absorbed. By the addition of dioxane and by heating, the product which has already crystallised out is taken into solution; the catalyst is filtered off and the filtrate is concentrated by evaporation. Recrystallisation from isopropanol and then from methanol yields pure 1-[2-(3-carbamoyl-4-hydroxy-phenoxy)-ethylamino]-3-[4-[2-(cyclopropylmethoxy)-ethyl]-phenoxy]-2-propanol, m.p. 149°–150°.

The starting material is produced in the following manner:

(44a) By application of the method described by Irvine et al., Synthesis 1972, 568, 2,5-dihydroxy-benzamide is converted, using an excess of acetone, into 2,3-dihydro-2,2-dimethyl-6-hydroxy-4H-1,3-benzoxazin-4-one, m.p. 215°–216°.

(44b) 70 g of 2,3-dihydro-2,2-dimethyl-6-hydroxy-4H-1,3-benzoxazin-4-one in 400 ml of acetonitrile with 100 g of potassium carbonate and 32 ml of chloroacetone are stirred under reflux for 30 hours. After the addition of a further 3.2 ml of chloroacetone, the reaction mixture is refluxed for a further 15–20 hours. The reaction mixture is filtered whilst still warm; the residue is thoroughly washed with acetone, and the combined filtrate is concentrated by evaporation. The crystalline residue is recrystallised from toluene and yields 2,3-dihydro-2,2-dimethyl-6-(2-oxopropoxy)-4H,-1,3-benzoxazin-4-one, m.p. 125°–126°.

(44c) 74 g of the resulting 2,3-dihydro-2,2-dimethyl-6-(2-oxopropoxy)-4H-1,3-benzoxazin-4-one in a mixture of 150 ml of dioxane and 450 ml of 2N hydrochloric acid are heated for 45 minutes on a water bath. The solvent is evaporated off, and the crystalline residue is triturated with water and then filtered off with suction. Recrystallisation from isopropanol yields 5-(2-oxo-propoxy)-salicylamide, which has a melting point of 152°–154°.

(44d) 55 g of benzylamine and 1.25 g of conc. sulfuric acid are added to a solution of 104.5 g of 5-(2-oxopropoxy)salicylamide in 1000 ml of methanol, and the mixture is hydrogenated, in the presence of 3.0 g of a Pt/C catalyst under normal conditions until 1 equivalent of hydrogen has been absorbed. The catalyst is filtered off, and the solution is then stirred up with about 10 g of pulverised calcium carbonate; the mixture is again filtered, and concentrated by evaporation. The oil remaining behind crystallises from isopropanol. Repeated recrystallisation from isopropanol yields 5-[2-(benzylamino)-propoxy]-salicylamide, m.p. 102°–104°.

(44e) A solution of 14.3 g of 1-[2-(cyclopropyl-methoxy)ethyl]-4-(2,3-epoxypropoxy)-benzene (German Offenlegungsschrift No. 2,649,605) and 16.3 g of 5-[2-(benzylamino)propoxy]-salicylamide in 200 ml of isopropanol is refluxed for 18 hours. The reaction mixture is concentrated by evaporation to leave crude 1-[N-[2-(3-carbamoyl-4-hydroxy-phenoxy)- ethyl]-benzylamino]-3-[4-[2-(cyclopropylmethoxy)e-thyl]-phenoxy]-2-propanol in the form of brown oil, which can be further processed without additional purification.

EXAMPLE 45

The following compounds are prepared in a manner analogous to Example 43:
1-[2-(3-carbamoyl-4-hydroxy-phenoxy)-ethylamino]-3-(4-methanesulphonylamino-phenoxy)-2-propanol;
1-[2-(3-carbamoyl-4-hydroxy-phenoxy)-1-methyl-ethylamino]-3-(4-methanesulphonylamino-phenoxy)-2-propanol.

EXAMPLE 46

A mixture of 11.5 g of 4-(2,3-epoxy-propoxy)cinnamic acid-N-methylamide and 7.4 g of 5-(2-aminoethoxy)salicylamide is dissolved in 50 ml of dimethyl sulfoxide heated to about 80°; the solution is stirred for 1 hour at 75°–85°, and is then poured into 500 ml of water. The resinous product which precipitates is separated and stirred up with 150 ml of ethyl acetate. The precipitating crystals are filtered off with suction, and recrystallised from a small amount of isopropanol to thus obtain 4-[3-[2-(3-carbamoyl-4-hydroxy-phenoxy)-ethylamino]-2-hydroxypropoxy]-N-methylcinnamic acid amide, m.p. 170°–171° (sinters from 148°).

EXAMPLE 47

A solution of 41 g of crude 1-[N-[2-(3-carbamoyl-4-hydroxy-phenoxy)-ethyl]-benzylamino]-3-[4-N-methyl-methanesulfonylamino)-phenoxy]-2-propanol in 410 ml of methanol is hydrogenated, in a manner analogous to that described in Example 4, in the presence of 4 g of palladium-on-charcoal catalyst and subsequently processed. The product obtained after recrystallisation from ethanol and methanol is 1-[2-(3-carbamoyl-4-hydroxy-phenoxy)-ethylamino]-3-[4-(N-methyl-methanesulphonylamino)-phenoxy]-2-propanol, m.p. 120°–121°.

The starting material is produced in the following manner:

(47a) 77 ml of methanesulfonic acid chloride are added dropwise in the course of about 30 minutes, with ice-cooling and stirring, to a solution of 103.7 g of 4-methylaminophenol sulfate in 330 ml of pyridine and 102 ml of N,N-diisopropylethylamine, and the mixture is stirred overnight at room temperature. The volatile constituents are evaporated off, and the residue is distributed between ethyl acetate and water; the organic phase is subsequently separated and concentrated by evaporation, and the crystalline residue is heated with 300 ml of 6N sodium hydroxide solution on a water-bath until completely dissolved. The solution is filtered, and the pH-value is adjusted to 2 with concentrated hydrochloric acid, whereupon 4-(N-methylsulfonylamino)-phenol precipitates in crystalline form. It is filtered off with suction and dried in vacuo at 80°, m.p. 135°–136°.

(47b) A mixture of 34.2 g of the compound obtained according to Examples (47a) 35.2 g of potassium carbonate and 125 ml of epichlorohydrin is stirred and refluxed for 2 hours. The suspension is filtered, the filtrate is concentrated by evaporation and distributed between ethyl acetate and water; the organic phase is then separated, dried over magnesium sulfate, and concentrated by evaporation to thus obtain 4-(2,3-epoxy-propoxy)-N-methylmethanesulfonanilide, m.p. 96°–100° (from methanol).

(47c) A solution of 19.0 g of the compound obtained according to Example (47b) and 21.4 g of 5-(2-benzylaminoethoxy)-salicylamide in 350 ml of isopropanol is refluxed for 5 hours. The product obtained after concentrating by evaporation is crude 1-[N-[2-(3-carbamoyl-4-hydroxyphenoxy)-ethyl]-benzylamino]-3-[4-(N-methyl-methanesulfonylamino)-phenoxy]-2-propanol in the form of viscous oil, which is further processed as such.

EXAMPLE 48

A solution of 23 g of crude 1-[N-[2-(3-carbamoyl-4-hydroxyphenoxy)ethyl]-benzylamino]-3-[4-(2-hydroxyethoxy)phenoxy]-2-propanol in 500 ml of methanol is hydrogenated, under normal conditions, with the addition of 2 g of 5% palladium on carbon catalyst, until hydrogen absorption has ceased. The catalyst is then removed by filtration and the filtrate is concentrated by evaporation under reduced pressure. The crystalline residue is stirred in a mixture of 50 ml of methanol and ether. The crystals so obtained are isolated by filtration and dried in vacuo, affording 1-[2-(3-carbamoyl-4-hydroxyphenoxy)ethylamino]-3-[4-(2-hydroxyethoxy)-phenoxy]-2-propanol with a melting point of 150°–151° C. Reaction with the equivalent amount of hydrogen chloride, as solution in methanol, affords the hydrochloride with a melting point of 205°–206° C.

The starting materials can be prepared as follows:

(a) 2-Benzyloxyethanol is reacted with methanesulfonyl chloride in pyridine/dichloromethane, in conventional manner, to give (2-benzyloxy)ethyl methanesulfonate.

(b) 400 ml of ethanol and 15.8 g of 85% potasssium hydroxide are added to 40.0 g of hydroquinone monobenzyl ether and the mixture is heated to form a solution. Then 66 g of crude (2-benzyloxy)ethyl methanesulfonate are added to this solution and the reaction mixture is stirred for 24 hours under reflux. The precipitated salts are removed by filtration while still warm and 4-[(2-benzyloxyethoxy)phenyl]-benzyl ether is obtained from the cooled filtrate. Melting point: 72°–73° C.

(c) A solution of 43.2 g of 4-[(2-benzyloxyethoxy)-phenyl]benzyl ether in 450 ml of tetrahydrofuran is hydrogenated with the addition of 9 g of 5% palladium on carbon catalyst. After absorption of 2 molar equivalents of hydrogen, the catalyst is removed by filtration and the filtrate is concentrated by evaporation. The resultant yellow oil gradually congeals to a crystalline solid. A sample is recrystallised from a small amount of isopropanol, affording pure 4-(2-hydroxyethoxy)phenol with a melting point of 98°–99° C.

(d) With stirring, 13 g of crude 4-(2-hydroxyethoxy)-phenol, 35 m of epichlorohydrin and 23.5 g of potassium carbonate are heated for 1½ hours to reflux temperature. The reaction mixture is filtered and the filtrate is concentrated by evaporation under reduced pressure. The residual oil gradually congeals to a crystalline solid, which is recrystallised from isopropanol, affording 1-(2,3-epoxypropoxy)-4-(2-hydroxyethoxy)benzene with a melting point of 65°–67° C. Working up of the mother liquor yields further crystalline product.

(e) A solution of 9.8 g of 1-(2,3-epoxypropoxy)-4-(2-hydroxyethoxy)benzene and 11.4 g of 5-[(2-benzylamino)ethoxy]-salicylamide in 100 ml of isopropanol is boiled under reflux for 10 to 12 hours. The solution is concentrated by evaporation under reduced pressure, affording 1-[N-[2-(3-carbamoyl-4-hydroxyphenoxy)ethyl]-benzylamino]-3-[4-(2-hydroxyethoxy)phenoxy]-2-propanol as a foam, which is further processed in this form.

We claim:

1. A compound of the formula

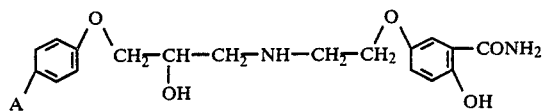

wherein A is 2-hydroxyethoxy or 2-(N-methylcarbamoyl)vinyl or a pharmaceutically acceptable, non-toxic acid addition salt thereof.

2. A compound as claimed in claim 1 which is 4-[3-[2-(3-carbamoyl-4-hydroxy-phenoxy)-ethylamino]-2-hydroxy-propoxy]-N-methylcinnamic acid amide or a pharmaceutically acceptable non-toxic acid addition salt thereof.

3. The compound of claim 1 which is 1-[2-(3-carbamoyl-4-hydroxy-phenoxy)-ethylamino]-3-[4-(2-hydroxyethoxy)phenoxy]-2-propanol or a pharmaceutically acceptable non-toxic acid addition salt thereof.

4. A pharmaceutical composition useful in the treatment of angina pectoris, cardiac arrhytmia as well as mycocardial insufficiency and as blood-pressure reducing agent comprising a therapeutically effective amount of a compound of formula I as defined in claim 1, or a pharmaceutically acceptable non-toxic acid addition salt thereof together with a pharmaceutically acceptable excipient.

5. A method for the treatment of angina pectoris, cardiac arrhytmia as well as myocardial insufficiency and for the reduction of blood-pressure in a warm-blooded animal which comprises the administration thereto of a therapeutically effective amount of a compound of formula I defined in claim 1 or a pharmaceutically acceptable non-toxic acid addition salt thereof.

* * * * *